United States Patent [19]

Müller et al.

[11] 4,329,347
[45] May 11, 1982

[54] CARDIOTONIC AND ANTITHROMBOTIC SULFUR-CONTAINING DERIVATIVES OF CARBOSTYRIL

[75] Inventors: Erich Müller; Josef Nickl; Josef Roch; Berthold Narr; Walter Haarmann; Johannes M. Weisenberger, all of Biberach an der Riss, Fed. Rep. of Germany

[73] Assignee: Boehringer Ingelheim GmbH, Ingelheim am Rhein, Fed. Rep. of Germany

[21] Appl. No.: 172,009

[22] Filed: Jul. 24, 1980

Related U.S. Application Data

[63] Continuation-in-part of Ser. No. 10,221, Feb. 8, 1979, abandoned.

[30] Foreign Application Priority Data

Aug. 4, 1979 [DE] Fed. Rep. of Germany ....... 2931741
Feb. 17, 1978 [DE] Fed. Rep. of Germany ....... 2806721
Dec. 9, 1978 [DE] Fed. Rep. of Germany ....... 2853314

[51] Int. Cl.³ .................. A61K 31/47; C07D 215/22
[52] U.S. Cl. .................... 424/251; 424/258; 424/274; 544/284; 544/316; 546/157; 546/158; 546/273; 548/265; 548/229; 548/159; 548/327; 548/486
[58] Field of Search ............... 546/157, 158; 424/258, 424/251; 544/284, 316

[56] References Cited

FOREIGN PATENT DOCUMENTS 2806721 8/1979 Fed. Rep. of Germany ...... 424/256
54-101387 9/1974 Japan ................................. 546/157

OTHER PUBLICATIONS

Nakagawa, et al., Chemical Abstracts, vol. 85, 94239q. (1976).

Primary Examiner—Mary C. Lee
Assistant Examiner—Diana G. Rivers
Attorney, Agent, or Firm—Hammond & Littell, Weissenberger and Muserlian

[57] ABSTRACT

Compounds of the formula

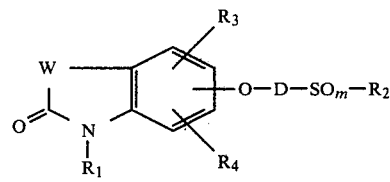

wherein
W is vinylene, methyl-vinylene, methylene or ethylene;
m is 0, 1 or 2;
D is straight or branched alkylene of 2 to 6 carbon atoms, straight or branched hydroxy-alkylene of 3 to 6 carbon atoms, or xylylene;
$R_1$ is hydrogen or alkyl of 1 to 3 carbon atoms;
$R_2$ is cycloalkyl of 3 to 6 carbon atoms, aryl of 6 to 10 carbon atoms, aralkyl of 7 to 11 carbon atoms, heteroaryl, heteroarlkyl, 1,2,4-triazolyl, triphenylmethyl, 4,5-bis-(p-chlorophenyl)-oxazol-2-yl, N-methyl-cyclohexylamino-carbonylmethyl,-amino-iminomethyl or, when m is 1 or D is hydroxyalkylene or xylylene, also alkyl of 1 to 6 carbon atoms; and
$R_3$ and $R_4$ are each hydrogen, halogen, alkyl of 1 to 4 carbon atoms, amino, acetylamino or nitro.

The compounds of the invention are useful as cardiotonics and as antithrombotics.

9 Claims, No Drawings

CARDIOTONIC AND ANTITHROMBOTIC SULFUR-CONTAINING DERIVATIVES OF CARBOSTYRIL

CROSS-REFERENCE TO RELATED APPLICATION

This application is a continuation-in-part of copending U.S. patent application Ser. No. 10,221 filed Feb. 8, 1979, now abandoned.

This invention relates to novel sulfur-containing derivatives of carbostyril and oxindole. This invention also relates to various methods of preparing these compounds, pharmaceutical compositions containing them as active ingredients, and methods of using them as cardiotonics and antithrombotics.

More particularly, the present invention relates to a novel class of compounds represented by the formula

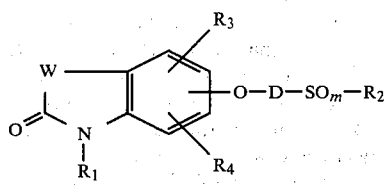

wherein

W is vinylene, methyl-vinylene, methylene or ethylene;

m is 0, 1 or 2;

D is straight or branched alkylene of 2 to 6 carbon atoms, straight or branched hydroxy-alkylene of 3 to 6 carbon atoms, or xylylene;

$R_1$ hydrogen or alkyl of 1 to 3 carbon atoms;

$R_2$ is cycloalkyl of 3 to 6 carbon atoms; aryl of 6 or 10 carbon atoms, aralkyl of 7 to 11 carbon atoms; heteroaryl of 4 to 9 carbon atoms or heteroaralkyl of 5 to 10 carbon atoms, each comprising one nitrogen atom and/or an oxygen or sulfur atom, or two nitrogen atoms in the ring, where the aromatic nucleus may optionally be mono-substituted by alkyl of 1 to 4 carbon atoms, hydroxyl, methoxy, amino, acetylamino, nitro, carboxyl, cyclohexyl, phenyl or halogen, and a mono-substituted phenyl moiety may, in addition, be mono- or di-substituted by alkyl of 1 to 4 carbon atoms and/or halogen, where said substituents on the phenyl moiety may be identical to or different from each other; 1, 2, 4-triazolyl; triphenylmethyl; 4,5-bis-(p-chlorophenyl)-oxazol-2-yl; N-methyl-cyclohexylamino-carbonylmethyl; amino-iminomethyl; or, when m is 1 or D is hydroxyalkylene or xylylene, also alkyl of 1 to 6 carbon atoms; and $R_3$ and $R_4$ which can be the same or different, are each hydrogen, halogen, alkyl of 1 to 4 carbon atoms, amino, acetylamino or nitro.

The term "halogen" in the definition of substituents $R_2$, $R_3$ and $R_4$ is primarily intended to include fluorine, chlorine, bromine and iodine.

Specific examples of variable substituents D, $R_1$, $R_2$, $R_3$ and $R_4$ in formula I are the following: D-ethylene, n-propylene, n-butylene, n-pentylene, n-hexylene, 1-methylethylene, 2-methylethylene, 1-methyl-n-propylene, 2-methyl-n-propylene, 3-methyl-n-propylene, 1-methyl-n-butylene, 2-methyl-n-butylene, 3-methyl-n-butylene, 4-methyl-n-butylene, 1-methyl-n-pentylene, 2-methyl-n-pentylene, 3-methyl-n-pentylene, 4-methyl-n-pentylene, 5-methyl-n-pentylene, 1,1-dimethylethylene, 1,2-dimethylethylene, 2,2-dimethylethylene, 1,1-dimethyl-n-propylene, 2,2-dimethyl-n-propylene, 3,3-dimethyl-n-propylene, 1,2-dimethyl-n-propylene, 1,3-dimethyl-n-propylene, 1,1-dimethyl-n-butylene, 2,2-dimethyl-n-butylene, 3,3-dimethyl-n-butylene, 4,4-dimethyl-n-butylene, 1,2-dimethyl-n-butylene, 1,3-dimethyl-n-butylene, 1,4-dimethyl-n-butylene, 2,3-dimethyl-n-butylene, 1-ethylethylene, 2-ethylethylene, 1-ethyl-n-propylene, 2-ethyl-n-propylene, 3-ethyl-n-proylene, 1-ethyl-n-butylene, 2-ethyl-n-butylene, 3-ethyl-n-butylene, 4-ethyl-n-butylene, 1-methyl-2-ethylethylene, 1-methyl-2-ethyl-n-propylene, 1methyl-3-ethyl-n-propylene, 1-methyl-2-propyl-ethylene, 1-propylethylene, 1-butylethylene, 1-propyl-n-propylene, 2-hydroxy-n-propylene, 2-hydroxy-n-butylene, 3-hydroxy-n-butylene, 2-hydroxy-n-pentylene, 3-hydroxy-n-pentylene, 4-hydroxy-n-pentylene, 2-hydroxy-n-hexylene, 3-hydroxy-n-hexylene, 1-methyl-2-hydroxy-n-propylene, 2-hydroxy-2-methyl-n-propylene, p-xylylene, o-xylylene or m-xylylene;

$R_1$—hydrogen, methyl, ethyl, propyl or isopropyl;

$R_2$—cyclopropyl, cyclobutyl, cyclopentyl, cyclohexyl, phenyl, benzyl, phenylethyl, naphthyl, naphthylmethyl, cyclohexylphenyl, biphenyl, triphenyl-methyl, N-methylcyclohexylaminocarbonylmethyl, amino-iminomethyl, pyridyl, pyridylmethyl, furfuryl, benzimidazolyl, benzthiazolyl, pyrimidyl, 1,2,4-triazolyl, quinolyl, quinazoline-4-one-yl, 4,5-bis-(p-chlorophenyl)-oxazole-2-yl, pyridyl-oxide, methylphenyl, dimethylphenyl, tert. butylphenyl, methyl-tert. butylphenyl, methylpyridyl, methoxyphenyl, dimethoxyphenyl, methoxypyridyl, hydroxyphenyl, dihydroxyphenyl, fluorophenyl, difluorophenyl, trifluorophenyl, fluoropyridyl, chlorophenyl, dichlorophenyl, trichlorophenyl, chloropyridyl, bromophenyl, dibromophenyl, aminophenyl, acetylaminophenyl, aminopyridyl, acetylaminopyridyl, nitrophenyl, carboxyphenyl, hydroxy-dichlorophenyl, hydroxy-dibromophenyl, amino-dichlorophenyl, amino-dibromophenyl, hydroxy-di-tert. butylphenyl, methoxy-fluorophenyl, methoxy-chlorophenyl, methoxy-bromophenyl, fluoromethylphenyl, chloromethylphenyl, or bromomethylphenyl;

$R_3$ and $R_4$—hydrogen, fluorine, chlorine, bromine, iodine, methyl, ethyl, propyl, isopropyl, butyl, tert. butyl, nitro, amino or acetylamino.

Thus, the present invention relates particularly to those compounds of the formula I, wherein W, D, m and $R_1$ have the meanings defined above in connection with formula I, $R_2$ is cyclohexyl, benzyl, naphthyl, pyridyl, pyrimidyl, 1,2,4-triazolyl, pyridyl-oxide, furfuryl, triphenylmethyl, quinolyl, benzimidazolyl, benzthiazolyl, quinazoline-4-one-yl, 4,5-bis-(p-chlorophenyl)oxazol-2-yl, N-methylcyclohexylamino-carbonylmethyl, amino-iminomethyl, phenyl optionally substituted by carboxyl, hydroxyl, methoxy, amino, acetylamino, nitro, cyclohexyl or phenyl; phenyl mono- or disubstituted by halogen and/or alkyl of 1 to 4 carbon atoms; or hydroxyphenyl, halophenyl or aminophenyl, each substituted by two halogen atoms or by two alkyl groups of 1 to 4 carbon atoms, $R_3$ is hydrogen, chlorine, bromine, methyl, amino, acetylamino or nitro; and $R_4$ is hydrogen.

A preferred sub-genus is constituted by those compounds of the formula I, wherein W is vinylene, methyl-vinylene or ethylene;

m is 0, 1 or 2;

D is alkylene of 2 to 5 carbon atoms or hydroxyalkylene of 3 to 5 carbon atoms;

$R_1$ is hydrogen;

$R_2$ is cyclohexyl, phenyl, benzyl, naphthyl, biphenyl, cyclohexylphenyl, pyridyl, methylphenyl, methoxyphenyl, fluorophenyl, chlorophenyl, dichlorophenyl, trichlorophenyl, bromophenyl, dibromophenyl, bromomethylphenyl, amino-dibromophenyl or hydroxy-di-tert. butylphenyl; and $R_3$ and $R_4$ are each hydrogen.

A further, particularly preferred sub-genus is constituted by those compounds of the formula I, wherein W is ethylene, vinylene or 2-methylvinylene;

m is 0, 1 or 2;

$R_1$, $R_3$ and $R_4$ are each hydrogen;

$R_2$ is cyclohexyl, phenyl, benzyl, naphthyl-(2), 2-methoxyphenyl, 4-chlorophenyl, 3,4-dichlorophenyl, 2,5-dichlorophenyl, 4-hydroxy-3,5-di-tert.-butylphenyl, 4-amino-3,5-dibromophenyl or pyridyl-(2); and D is ethylene, n-propylene, n-butylene or 2-hydroxy-n-propylene.

The compounds embraced by formula I may be prepared by the following methods:

METHOD A

By reacting a hydroxy-compound of the formula

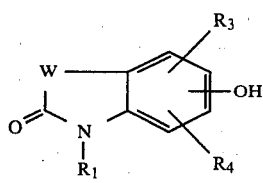

(II)

wherein $R_1$, $R_3$, $R_4$ and W have the same meanings as in formula I, or a salt thereof formed with an inorganic or tertiary organic base, with a compound of general formula

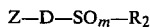 Z—D—SO$_m$—R$_2$    (III)

wherein

D, $R_2$ and m have the same meanings as in formula I, and

Z is a nucleophilic exchangeable substituent such as halogen or a sulfonic acid ester group, for instance, chlorine, bromine, iodine, p-toluenesulfonyloxy or methanesulfonyloxy.

The reaction is advantageously carried out in a suitable solvent such as dioxane, tetrahydrofuran, chloroform or toluene, preferably, however, in an anhydrous aprotic solvent such as acetone, dimethylformamide or dimethylsulfoxide, and optionally in the presence of an alkali metal base, such as sodium carbonate, potassium carbonate or sodium hydroxide, at temperatures between 0° C. and the boiling point of the solvent, for examples at temperatures between 0° and 100° C., preferably, however, at temperatures between 10° and 50° C. The reaction can, however, also be carried out without a solvent.

METHOD B

For the preparation of a compound of the formula I wherein m is 1 or 2, by oxidizing a compound of the formula

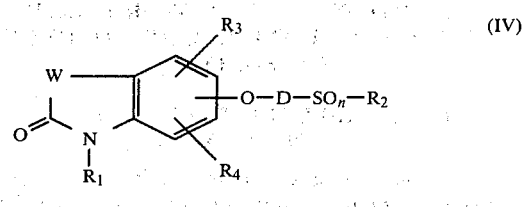

wherein $R_1$, $R_2$, $R_3$, $R_4$, D and W have the same meanings as in formula I, and n is 0 or 1.

The oxidation is preferably carried out in a solvent, such as water, water/pyridine, ethanol, methanol, acetone, formic acid, glacial acetic acid, dilute sulfuric acid or trifluoro acetic acid, and at temperatures between −80 and 100° C., depending upon the particular oxidizing agent which is used.

For the preparation of a compound of the formula I wherein m is 1, the oxidation is carried out with one equivalent of the oxidizing agent; for instance with hydrogen peroxide in glacial acetic acid or formic acid at 0° to 20° C. of in acetone at 0° to 60° C.; with a peracid such as performic acid in glacial acetic acid or trifluoro acetic acid at 0° to 50° C.; with sodium metaperiodate in aqueous methanol or ethanol at 15° to 25° C.; with N-bromo-succinimide in ethanol; with tert. butyl-hypochlorite in methanol at −80° to −30° C.; with iodobenzene dichloride in aqueous pyridine at 0° to 50° C.; with nitric acid in glacial acetic acid at 0° to 20° C.; with chromic acid in glacial acetic acid or in acetone at 0° to 20° C.; or with sulfuryl chloride in methylene chloride at −70° C., where the obtained thioetherchlorine-complex is hydrolyzed with aqueous ethanol.

For the preparation of a compound of the formula I wherein m is 2, the oxidation is carried out with one or two or more equivalents of the oxidizing agent; for instance, with hydrogen peroxide in glacial acetic acid or formic acid at 20° to 100° C. or in acetone at 0° to 60° C.; with a peracid such as performic acid or m-chloroperbenzoic acid in glacial acetic acid, trifluoro acetic acid or chloroform at temperatures between 0° and 50° C.; with nitric acid in glacial acetic acid at 0° to 20° C.; with chromic acid or potassium permanganate in glacial acetic acid, water/sulfuric acid or in acetone at 0° to 20° C. If n in formula IV is 0, the reaction is preferably carried out with two or more equivalents of the corresponding oxidizing agent, and accordingly with at least one equivalent if n is 1.

METHOD C

For the preparation of a compound of the formula I wherein m is 0, by reacting a compound of the formula

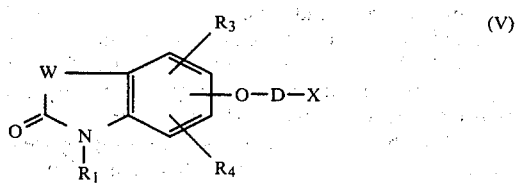

with a compound of the formula

Y—R₂ (VI)

where $R_1$, $R_2$, $R_3$, $R_4$, D and W have the same meanings as in formula I, and one of X and Y in formulas V and VI, respectively, is mercapto while the other is a nucleophilic exchangeable substituent, such as halogen or a sulfonic acid ester group, for instance chlorine, bromine iodine, p-toluenesulfonyloxy or methanesulfonyloxy, or X, together with the neighboring hydroxyl group of D, is an epoxide group and Y is mercapto. The reaction is advantageously carried out in a suitable solvent such as dioxane, tetrahydrofuran, chloroform or toluene, but preferably in an anhydrous aprotic solvent such as acetone, dimethylformamide or dimethylsulfoxide, and optionally in the presence of an alkali metal base such as sodium carbonate, potassium carbonate or sodium hydroxide at temperatures between 0° C. and the boiling point of the solvent, for instance, at temperatures between 0° and 100° C., but preferably at temperatures between 10° and 50° C. However, the reaction can also be carried out without a solvent.

METHOD D

For the preparation of a carbostyril of the formula I wherein $R_1$ is other than hydrogen, by reacting a compound of the formula

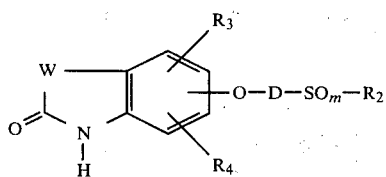

(VII)

wherein $R_2$, $R_3$, $R_4$, D, W and m have the same meanings as in formula I, or an alkali metal salt thereof, with a compound of the formula

Z—R₁ (VIII)

wherein $R_1$ has the same meanings as in formula I, and

Z is a nucleophilic exchangeable group, such as halogen or a sulfonic acid ester group, for instance, chlorine, bromine, iodine, p-toluene-sulfonyloxy or methanesulfonyloxy.

The alkylation is advantageously carried out in an aprotic solvent such as acetone, dimethylformamide or dimethylsulfoxide in the presence of an inorganic base such as potassium carbonate, sodium hydroxide, sodium hydride or potassium hydroxide, or in the presence of an alcoholate such as sodium methylate, at temperatures between 0° and 50° C., but preferably at temperatures between 10° and 25° C. Suitable alkylating agents of the formula VIII are especially alkyl halides, such as methyl iodide, or isopropyl bromide, or dialkyl sulfates such as dimethyl or diethyl sulfate.

METHOD E

For the preparation of a carbostyril of the formula I wherein W is vinylene, by dehydrogenating a 3,4-dihydrocarbostyril of the formula

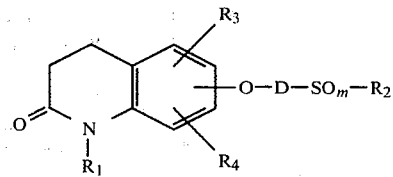

(IX)

wherein $R_1$, $R_2$, $R_3$, $R_4$, D and m have the same meanings as in formula I.

The dehydrogenation is carried out in the presence of a dehydrogenating agent, for instance an oxidizing agent such as 2,3-dichloro-5,6-dicyano-benzoquinone, chloranil or a nobel metal catalyst such as palladium-on-charcoal, preferably in an inert solvent such as dioxane or mesitylene, at elevated temperatures, for example at temperatures between 100° and 200° C., but preferably at the boiling point of the solvent.

METHOD F

For the preparation of a carbostyril of the formula I wherein W is ethylene and m is 0 or 2, by hydrogenating a carbostyril of the formula

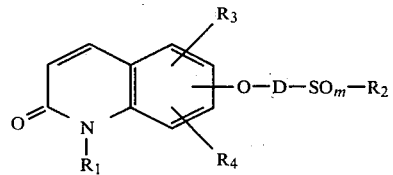

(X)

wherein $R_1$, $R_2$, $R_3$, $R_4$, D and m have the same meanings as in formula I.

The hydrogenation is carried out in a suitable solvent, such as ethanol, ethyl acetate, glacial acetic acid or dioxane, with catalytically activated hydrogen, for example with hydrogen in the presence of a hydrogenation catalyst such as palladium-on-charcoal, platinum, Raney nickel, Raney cobalt or dirhenium heptasulfide, at temperatures between 0° and 50° C., but preferably at room temperature and at a hydrogen pressure of 1 to 5 bar.

Some of the starting compounds of the formulas II to X are known from the literature, and those which are not known can be obtained according to known methods. For example a 6-, 7- or 8-hydroxy-3,4-dihydro-carbostyril of the formula II can be obtained by acylation of a corresponding aniline derivative with a corresponding β-halo-carboxylic acid derivate and subsequent cyclization according to the method described by Friedel-Crafts [see J. Chem. Soc. 1955, 743–744; Chem. Pharm. Bull. 1961, 970–975; and Ber. Dtsch. Chem. Ges. 60, 858 (1927)]. A 5-hydroxy-3,4-dihydrocarbostyril of the formula II can be obtained by cyclization of a corresponding 2-(β-cyanoethyl)-cyclohexane-1,3-dione derivative and subsequent aromatization, for example with N-bromo-succinimide (see Chem. and Ind. 1970, 1435).

The preparation of the corresponding hydroxy-carbostyrils of general formula II is known from the literature [see for example J. Amer. Chem. Soc. 72, 346 (1950), and ibid 76, 2402 (1954); or J. Org. Chem. 33, 1089 (1968), and, ibid 36, 3493 (1971)]. Furthermore, the preparation of 5-hydroxyoxindole is described in J. Chem. Soc. 1961, 2723.

The starting compounds of the formulas IV, V, VII, IX and X can be obtained by alkylation of a corresponding hydroxy derivative and optionally by subsequent oxidation.

The following examples illustrate the present invention and will enable others skilled in the art to understand it more completely. It should be understood, however, that the invention is not limited solely to the particular examples given below.

EXAMPLE 1

6-[4-(2-Pyridylmercapto)-butoxy]-3,4-dihydro-carbostyril 14.4 gm (0.13 mol) of 2-mercapto-pyridine and 17.9 gm (0.13 mol) of potassium carbonate were stirred into 360 ml of dimethylsulfoxide which had been dried over a molecular sieve, and the solution was admixed with 36 gm (0.12 mol) of 6-(4-bromo-butoxy)-3,4-dihydro-carbostyril (m.p. 142°-147° C.; prepared from 6-hydroxy-carbostyril and 1,4-dibromo-butane). The mixture was stirred for 15 hours at about 25° C., then poured into 3.6 liters of water, and the aqueous mixture was stirred for 30 minutes. The precipitate formed thereby was collected by suction filtration, thoroughly washed with water, dried and recrystallized from xylene in the presence of activated charcoal, yielding 32 gm (81.2% of theory) of a light yellow crystalline product having a melting point of 123°-124.5° C. It was identified to be the compound of the formula

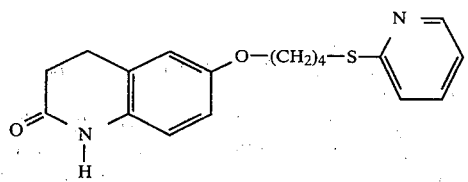

EXAMPLE 2

6-[4-(Pyridyl-sulfinyl)-butoxy]-3,4-dihydro-carbostyril 32.8 gm (0.1 mol) of 6-[4-(2-pyridyl-mercapto)-butoxy]-3,4-dihydro-carbostyril were dissolved in 330 ml of glacial acetic acid, and 10.2 gm (0.105 mol) of 35% hydrogen peroxide were added. The solution was stirred for 15 hours at about 20° C. The glacial acetic acid was distilled off at 60° C. in vacuo, the residue was washed with ether, and the thus obtained crude product was recrystallized twice from xylene in the presence of activated charcoal. Colorless crystals with a melting point of 144.5°-146° C. were obtained. Yield: 27.5 gm (79.8% of theory).

EXAMPLE 3

6-[4-(2-Pyridyl-sulfonyl)-butoxy]-3,4-dihydro-carbostyril 5 gm (0.015 mol) of 6-[4-(2-pyridyl-mercapto)-butoxy]-3,4-dihydro-carbostyril were dissolved in 50 ml of glacial acetic acid, and 4.5 gm (0.045 mol) of 35% hydrogen peroxide were added. After stirring for 40 hours at about 25° C., the glacial acetic acid was distilled off at 60° C. in vacuo. The solid residue was washed with ether and recrystallized from xylene in the presence of activated charcoal. Colorless crystals with a melting point of 123.8°-125° C. were obtained.

Yield: 3.8 gm (70.3% of theory).

EXAMPLE 4

6-(4-Phenylsulfinyl-butoxy)-3,4-dihydro-carbostyril 32.6 gm (0.2 mol) of 6-hydroxy-3,4-dihydro-carbostyril [see F. F. Mayer et al., Ber. Dtsch. Chem. Ges. 60, 858 (1927)] and 27.6 gm (0.2 mol) of potassium carbonate were stirred for 5 minutes in 600 ml of dimethylsulfoxide which had been dried over a molecular sieve, and then 52.2 gm of 4-phenylsulfinyl-butyl bromide (0.2 mol) (prepared from thiophenol and 1,4-dibromo-butane and subsequent oxidation with hydrogen peroxide in glacial acetic acid analogous to Example 2; oily substance, solidified upon standing in the refrigerator) were added. After stirring it for 15 hours at 25° C., the reaction mixture was poured into 6 liters of water. After stirring the aqueous mixture for 30 minutes more, the precipitated product was suction-filtered off and thoroughly washed with water. After drying, the filter cake was recrystallized from about 600 ml of xylene in the presence of charcoal. White crystals with a melting point of 144.5°-145.5° C. were obtained.

Yield: 49 gm (71.3% of theory).

EXAMPLE 5

6-(4-Phenylmercapto-butoxy)-3,4-dihydro-carbostyril

Prepared analogous to Example 4 from 6-hydroxy-3,4-dihydro-carbostyril and 4-(phenylmercapto)-butyl bromide (b.p. 96°-103° C. at 0.02 mm Hg; prepared from thiophenol and 1.4-dibromo butane).

M.p.: 121.5°-123° C.

Yield: 75.6% of theory.

EXAMPLE 6

6-(4-Phenylsulfonyl-butoxy)-3,4-dihydro-carbostyril

Prepared analogous to Example 4 from 6-hydroxy-3,4-dihydro-carbostyril and 4-phenylsulfonyl-butyl bromide (prepared from 4-(phenylmercapto)-butyl bromide by oxidation analogous to Example 3).

M.p.: 157.5°-158° C.

Yield: 65.1% of theory.

EXAMPLE 7

6-[4-(4-Fluorophenyl-mercapto)-butoxy]-3,4-dihydro-carbostyril

Prepared analogous to Example 1 from 6-(4-bromo-butoxy)-3,4-dihydro-carbostyril (m.p. 142°-147° C.) and 4-fluorothiophenol.

M.p.: 139°-140° C.

Yield: 93.1% of theory.

EXAMPLE 8

6-[4-(4-Fluorophenyl-sulfinyl)-butoxy]-3,4-dihydro-carbostyril

Prepared analogous to Example 2 from 6-[4-(4-fluorophenyl-mercapto)-butoxy]-3,4-dihydro-carbostyril.

M.p.: 184.5°-186° C.

Yield: 88% of theory.

EXAMPLE 9

6-[4-(4-Methylphenyl-mercapto)-butoxy]-3,4-dihydro-carbostyril

Prepared analogous to Example 1 from 6-(4-chlorobutoxy)-3,4-dihydro-carbostyril (m.p. 147°-148° C.) and 4-methyl-thiophenol.

M.p. 120°–121° C.
Yield: 91% of theory.

EXAMPLE 10

6-[4-(4-Methylphenyl-sulfinyl)-butoxy]-3,4-dihydro-carbostyril

Prepared analogous to Example 2 from 6-[4-(4-methylphenyl-mercapto)-butoxy]-3,4-dihydro-carbostyril and hydrogen peroxide.
M.p.: 149.5°–150° C.
Yield: 97% of theory.

EXAMPLE 11

6-[4-(3-Methylphenyl-mercapto)-butoxy]-3,4-dihydro-carbostyril

Prepared analogous to Example 1 from 6-(4-chloro-butoxy)-3,4-dihydro-carbostyril (m.p. 147°–148° C.) and 3-methyl-thiophenol.
M.p.: 95°–96° C.
Yield: 91% of theory.

EXAMPLE 12

6-[4-(3-Methylphenyl-sulfinyl)-butoxy]-3,4-dihydro-carbostyril

Prepared analogous to Example 2 from 6-[4-(3-methylphenyl-mercapto)-butoxy]-3,4-dihydro-carbostyril and hydrogen peroxide.
Wax-like resin.
Yield: 95% of theory.
$R_f$-value: 0.48 (thin-layer chromatogram on silica gel—eluant: benzene/ethanol/conc. ammonia=75/25/1).

EXAMPLE 13

6-[4-(4-Chlorophenyl-mercapto)-butoxy]-3,4-dihydro-carbostyril

Prepared analogous to Example 1 from 6-(4-chloro-butoxy)-3,4-dihydro-carbostyril (m.p. 147°–148° C.) and 4-chloro-thiophenol.
M.p.: 144°–146° C.
Yield: 88% of theory.

EXAMPLE 14

6-[4-(4-Chlorophenyl-sulfinyl)-butoxy]-3,4-dihydro-carbostyril

Prepared analogous to Example 2 from 6-[4-(4-chlorophenyl-mercapto)-butoxy]-3,4-dihydro-carbostyril and hydrogen peroxide.
M.p.: 148°–149.5° C.
Yield: 70% of theory.

EXAMPLE 15

6-[4-(3,4-Dichlorophenyl-mercapto)-butoxy]-3,4-dihydro-carbostyril

Prepared analogous to Example 1 from 6-(4-chloro-butoxy)-3,4-dihydro-carbostyril (m.p. 147°–148° C.) and 3,4-dichloro-thiophenol.
M.p.: 116.5°–118° C.
Yield: 87% of theory.

EXAMPLE 16

6-[4-(3,4-Dichlorophenyl-sulfinyl)-butoxy]-3,4-dihydro-carbostyril

Prepared analogous to Example 2 from 6-[4-(3,4-dichlorophenyl-mercapto)-butoxy]-3,4-dihydro-carbostyril and hydrogen peroxide.
M.p.: 106.5°–108° C. (from toluene).
Yield: 74% of theory.
M.p.: 147°–149° C. (from ethanol).

EXAMPLE 17

6-[4-(2-Methoxyphenyl-mercapto)-butoxy]-3,4-dihydro-carbostyril

Prepared analogous to Example 1 from 6-(4-bromo-butoxy-3,4-dihydro-carbostyril (m.p. 142°–147° C.) and 2-methoxy-thiophenol.
M.p.: 130.5°–133° C.
Yield: 74% of theory.

EXAMPLE 18

6-[4-(2-Methoxyphenyl-sulfinyl)-butoxy]-3,4-dihydro-carbostyril

Prepared analogous to Example 2 from 6-[4-(2-methoxyphenyl-mercapto)-butoxy]-3,4-dihydro-carbostyril and hydrogen peroxide.
M.p.: 162°–163° C.
Yield: 62% of theory.

EXAMPLE 19

6-[4-(3-Methoxyphenyl-mercapto)-butoxy]-3,4-dihydro-carbostyril

Prepared analogous to Example 1 from 6-(4-bromo-butoxy)-3,4-dihydro-carbostyril (m.p. 142°–147° C.) and 3-methoxy-thiophenol.
M.p.: 93.5°–97° C. Yield: 61% of theory.

EXAMPLE 20

6-[4-(3-Methoxyphenyl-sulfinyl)-butoxy]-3,4-dihydro-carbostyril

Prepared analogous to Example 2 from 6-[4-(3-methoxyphenyl-mercapto)-butoxy]-3,4-dihydro-carbostyril and hydrogen peroxide.
M.p.: 147°–148° C.
Yield: 49% of theory.

EXAMPLE 21

6-[4-(4-Methoxyphenyl-mercapto)-butoxy]-3,4-dihydro-carbostyril

Prepared analogous to Example 1 from 6-(4-bromo-butoxy)-3,4-dihydro-carbostyril (m.p. 142°–147° C.) and 4-methoxy-thiophenol.
M.p.: 130.5°–133° C.
Yield: 82% of theory.

EXAMPLE 22

6-[4-(4-Methoxyphenyl-sulfinyl)-butoxy]-3,4-dihydro-carbostyril

Prepared analogous to Example 2 from 6-[4-(4-methoxyphenyl-mercapto)-butoxy]-3,4-dihydro-carbostyril and hydrogen peroxide.
M.p.: 132°–133° C.
Yield: 71% of theory.

EXAMPLE 23

6-[4-(3,4-Dimethoxyphenyl-mercapto)-butoxy]-3,4-dihydro-carbostyril

Prepared analogous to Example 1 from 3,4-dimethoxy-thiophenol and 6-(4-chlorobutoxy)-3,4-dihydro-carbostyril [prepared from 6-hydroxy-carbostyril (see F. Mayer et al. in Ber. Dtsch. Chem. Ges. 60, 858 (1927) and 4-chloro-butyl benzenesulfonate].
M.p.: 117°–119° C.
Yield: 73% of theory.

EXAMPLE 24

6-[4-(3,4-dimethoxyphenyl-sulfinyl)-butoxy]-3,4-dihydro-carbostyril

Prepared analogous to Example 2 from 6-[4-(3,4-dimethoxyphenyl-mercapto)-butoxy]-3,4-dihydro-carbostyril and hydrogen peroxide.
M.p.: 145°–147° C.
Yield: 79% of theory.

EXAMPLE 25

6-[4-(3,4-Dimethoxyphenyl-sulfonyl)-butoxy]-3,4-dihydro-carbostyril

Prepared analogous to Example 3 from 6-[4-(3,4-dimethoxy-phenyl-mercapto)-butoxy]-3,4-dihydro-carbostyril and hydrogen peroxide.
M.p.: 158°–160° C.
Yield: 62% of theory.

EXAMPLE 26

6-[4-(4-Biphenylyl-mercapto)-butoxy]-3,4-dihydro-carbostyril

Prepared analogous to Example 1 from 4-phenyl-thiophenol and 6-(4-bromo-butoxy)-3,4-dihydro-carbostyril.
M.p.: 179.5°–181° C.
Yield: 74% of theory.

EXAMPLE 27

6-[4-(4-Biphenylyl-sulfinyl)-butoxy]-3,4-dihydro-carbostyril

Prepared analogous to Example 2 from 6-[4-(4-biphenyl-mercapto)-butoxy]-3,4-dihydro-carbostyril and hydrogen peroxide.
M.p.: 192°–192.5° C.
Yield: 86% of theory.

EXAMPLE 28

6-[4-(2-Naphthyl-mercapto)-butoxy]-3,4-dihydro-carbostyril

Prepared analogous to Example 1 from 2-naphthyl-mercaptan and 6-(4-bromo-butoxy)-3,4-dihydro-carbostyril.
M.p.: 108.5°–109.5° C.
Yield: 48% of theory.

EXAMPLE 29

6-[4-(2-Naphthyl-sulfinyl)-butoxy]-3,4-dihydro-carbostyril

Prepared analogous to Example 2 from 6-[4-(2-naphthyl-mercapto)-butoxy]-3,4-dihydro-carbostyril and hydrogen peroxide.
M.p.: 147.5°–148.5° C.
Yield: 57% of theory.

EXAMPLE 30

6-[5-(2-Pyridyl-sulfinyl)-pentoxy]-3,4-dihydro-carbostyril

Prepared analagous to Example 2 from 6-[5-(2-pyridyl-mercapto)-pentoxy]-3,4-dihydro-carbostyril and hydrogen peroxide.
M.p.: 116°–118° C.
Yield: 69% of theory.

EXAMPLE 31

6-(2-Methylsulfinyl-ethoxy)-3,4-dihydro-carbostyril 1.42 gm (0.006 mol) of 6-(2-methylmercapto-ethoxy)-3,4-dihydro-carbostyril were suspended in 12 ml of methanol, and a solution of 1.71 gm (0.008 mol) of sodium metaperiodate in 8 ml of water was added. The reaction mixture was stirred for 1.5 hours; at the beginning a distinct warming of the reaction mixture was noted. Subsequently, the mixture was diluted with a little water and exhaustively extracted with chloroform. The evaporation residue of the chloroform extract was recrystallized from ethyl acetate by addition of a little ethanol.
M.p.: 129°–131.5° C.
Yield: 70% of theory.

EXAMPLE 32

6-[5-(2-Pyridyl-sulfonyl)-pentoxy]-3,4-dihydro-carbostyril

Prepared analogous to Example 3 from 6-[5-(2-pyridyl-mercapto)-pentoxy]-3,4-dihydro-carbostyril and hydrogen peroxide.
M.p.: 113.5°–115.0° C.
Yield: 71% of theory.

EXAMPLE 33

6-(4-Methylsulfinyl-butoxy)-3,4-dihydro-carbostyril

Prepared analogous to Example 2 from 6-(4-methylmercapto-butoxy)-3,4-dihydro-carbostyril and hydrogen peroxide.
M.p.: 128.5°–130.5° C.
Yield: 58% of theory.

EXAMPLE 34

7-(4-Phenylsulfonyl-butoxy)-carbostyril

Prepared analogous to Example 3 from 7-(4-phenyl-mercapto-butoxy)-carbostyril and hydrogen peroxide.
M.p.: 199°–201° c.
Yield: 85% of theory.

EXAMPLE 35

6-(4-Cyclohexylmercapto-butoxy)-3,4-dihydro-carbostyril

Prepared analogous to Example 1 from cyclohexylmercaptan and 6-(4-chloro-butoxy)-3,4-dihydro-carbostyril
m.p. 147°–148° C.).
M.p.: 114°–115° C.
Yield: 80% of theory.

EXAMPLE 36

6-(4-Cyclohexylsulfinyl-butoxy)-3,4-dihydro-carbostyril

Prepared analogous to Example 2 from 6-(4-cyclohexyl-mercapto-butoxy)-3,4-dihydro-carbostyril and hydrogen peroxide.
M.p.: 153°–155.5° C.
Yield: 63% of theory.

EXAMPLE 37

6-(4-Benzyl-mercapto-butoxy)-3,4-dihydro-carbostyril

Prepared analogous to Example 1 from benzyl mercaptan and 6-(4-chloro-butoxy)-3,4-dihydro-carbostyril.
M.p.: 77.5°–78.5° C.
Yield: 90% of theory.

EXAMPLE 38

6-(4-Benzylsulfinyl-butoxy)-3,4-dihydro-carbostyril

Prepared analogous to Example 2 from 6-(4-benzyl-mercapto-butoxy)-3,4-dihydro-carbostyril and hydrogen peroxide.
M.p.: 141.5°–142° C.
Yield: 95% of theory.

EXAMPLE 39

6-[4-(2-Furylmethyl-mercapto)-butoxy]-3,4-dihydro-carbostyril

Prepared analogous to Example 1 from furfuryl-mercaptan and 6-(4-bromo-butoxy)-3,4-dihydro-carbostyril (m.p. 142°–147° C.).
M.p. 79°–80° C.
Yield: 64% of theory.

EXAMPLE 40

6-[4-(2-Furylmethyl-sulfinyl)-butoxy]-3,4-dihydro-carbostyril

Prepared analogous to Example 2 from 6-[4-(2-furylmethyl-mercapto)-butoxy]-3,4-dihydro-carbostyril and hydrogen peroxide.
M.p.: 135°–136° C.
Yield: 60% of theory.

EXAMPLE 41

6-[4-(N-Oxido-2-pyridyl-mercapto)-butoxy]-3,4-dihydro-carbostyril

Prepared analogous to Example 1 from 6-(4-bromo-butoxy)-3,4-dihydro-carbostyril and 2-mercapto-pyridine-N-oxide.
M.p.: 179.5°–181° C.
Yield: 65% of theory.

EXAMPLE 42

6-[4-(2-Pyrimidyl-mercapto)-butoxy]-3,4-dihydro-carbostyril

Prepared analogous to Example 1 from 6-(4-chloro-butoxy)-3,4-dihydro-carbostyril (m.p.: 147°–148° C.) and 2-mercapto-pyrimidine.
M.p.: 154°–156° C.
Yield: 79% of theory.

EXAMPLE 43

6-[4-(2-Pyrimidyl-sulfinyl)-butoxy]-3,4-dihydro-carbostyril

Prepared analogous to Example 2 from 6-[4-(2-pyrimidyl-mercapto)-butoxy]-3,4-dihydro-carbostyril and hydrogen peroxide.
M.p. 154°–156° C.
Yield: 36% of theory.

EXAMPLE 44

6-[4-(4-Pyridyl-mercapto)-butoxy]-3,4-dihydro-carbostyril 3.0 gm of 6-(4-bromo-butoxy)-3,4-dihydro-carbostyril were added to a solution of 1.3 gm of 4-mercapto-pyridine and 2.3 gm of a 30% sodium methylate solution in 15 ml of methanol, and the mixture was stirred for 14 hours at room temperature. Subsequently, the reaction solution was diluted with 20 ml of water and the resulting precipitate was recrystallized from ethanol.
M.p.: 128°–129° C.
Yield: 1.6 gm (49% of theory).

EXAMPLE 45

6-[4-(2-Benzimidazolyl-mercapto)-butoxy]-3,4-dihydro-carbostyril

Prepared analogous to Example 1 from 6-(4-chlorobutoxy)-3,4-dihydro-carbostyril (m.p. 147°–148° C.) and 2-mercapto-benzimidazole.
M.p. 100°–103° C.
Yield: 45% of theory.

EXAMPLE 46

6-[4-(2-Benzimidazolyl-sulfinyl)-butoxy]-3,4-dihydro-carbostyril

Prepared analogous to Example 2 from 6-[4-(2-benzimidazolyl-mercapto)-butoxy]-3,4-dihydrocarbostyril and hydrogen peroxide.
M.p.: 180°–182° C.
Yield: 36% of theory.

EXAMPLE 47

6-[4-(2-Benzthiazolyl-mercapto)-butoxy]-3,4-dihydro-carbostyril

Prepared analogous to Example 1 from 6-(4-chlorobutoxy)-3,4-dihydro-carbostyril (m.p.: 147°–148° C.) and 2-mercapto-benzthiazole.
M.p.: 157°–158° C.
Yield: 70% of theory.

EXAMPLE 48

6-[4-(2-Benzthiazolyl-sulfinyl)-butoxy]-3,4-dihydro-carbostyril

Prepared analogous to Example 2 from 6-[4-(2-benzthiazolyl-mercapto)-butoxy]-3,4-dihydro-carbostyril and hydrogen peroxide.
M.p.: 183°–184° C.
Yield: 69% of theory.

EXAMPLE 49

6-(2-Phenylmercapto-ethoxy)-3,4-dihydro-carbostyril

Prepared analogous to Example 1 from thiophenol and 6-(2-chloro-ethoxy)-3,4-dihydro-carbostyril (m.p. 152.5° to 153.5° C.).

M.p.: 132°–133.5° C.
Yield: 91% of theory.

EXAMPLE 50

6-(2-Phenylsulfinyl-ethoxy)-3,4-dihydro-carbostyril

Prepared analogous to Example 2 from 6-(2-phenyl-mercapto-ethoxy)-3,4-dihydro-carbostyril and hydrogen peroxide.
M.p.: 171°–172° C.
Yield: 84% of theory.

EXAMPLE 51

6-(2-Phenylsulfonyl-ethoxy)-3,4-dihydro-carbostyril

Prepared analogous to Example 3 from 6-(2-phenyl-mercapto-ethoxy)-3,4-dihydro-carbostyril and hydrogen peroxide.
M.p.: 185°–186° C.
Yield: 94% of theory.

EXAMPLE 52

6-(3-Phenylmercapto-propoxy)-3,4-dihydro-carbostyril

Prepared analogous to Example 1 from 6-(3-bromo-propoxy)-3,4-dihydro-carbostyril (m.p. 111°–118° C.) and thiophenol.
M.p.: 111°–112° C.
Yield: 77% of theory.

EXAMPLE 53

6-(3-Phenylsulfinyl-propoxy)-3,4-dihydro-carbostyril

Prepared analogous to Example 2 from 6-[3-(phenyl-mercapto)-propoxy]-3,4-dihydro-carbostyril and hydrogen peroxide.
M.p.: 131.5°–133.5° C.
Yield: 67% of theory.

EXAMPLE 54

1-Methyl-6-(4-phenylmercapto-butoxy)-3,4-dihydro-carbostyril 16.2 gm of 6-(4-phenylmercapto-butoxy)-3,4-dihydro-carbostyril were dissolved in 100 ml of dimethylformamide, and 4.8 gm of a 50% sodium hydride suspension in paraffin oil were added to this solution. After addition of 12.5 ml of methyl iodide, the mixture was stirred for 3 hours at room temperature, diluted with water and extracted with chloroform. The evaporation residue of the chloroform extract was recrystallized with methanol in the presence of activated charcoal.
M.p.: 79.5°–80.5° C.
Yield: 71% of theory.

EXAMPLE 55

1-Methyl-6-(4-phenylsulfinyl-butoxy)-3,4-dihydro-carbostyril

Prepared analogous to Example 2 from 1-methyl-6-(4-phenyl-mercapto-butoxy)-3,4-dihydro-carbostyril and hydrogen peroxide.
M.p.: 82°–82.5° C.
Yield: 60% of theory.

EXAMPLE 56

1-Methyl-6-(4-phenylsulfonyl-butoxy)-3,4-dihydro-carbostyril

Prepared analogous to Example 3 from 1-methyl-6-(4-phenyl-mercapto-butoxy)-3,4-dihydro-carbostyril and hydrogen peroxide.
M.p.: 108°–109° C.
Yield: 49% of theory.

EXAMPLE 57

6-(6-Phenylmercapto-hexoxy)-3,4-dihydro-carbostyril

Prepared analogous to Example 1 from 6-(6-bromohexoxy)-3,4-dihydro-carbostyril (m.p. 107.5°–108° C.) and thiophenol.
M.p.: 112.5°–113° C.
Yield: 34% of theory.

EXAMPLE 58

6-(6-Phenylsulfinyl-hexoxy)-3,4-dihydro-carbostyril

Prepared analogous to Example 2 from 6-(6-phenyl-mercapto-hexoxy)-3,4-dihydro-carbostyril and hydrogen peroxide.
M.p.: 119.5°–121.5° C.
Yield: 35% of theory.

EXAMPLE 59

6-(2-Hydroxy-3-phenylmercapto-propoxy)-3,4-dihydro-carbostyril 4.11 gm (0.04 mol) of thiophenol were added to a suspension of 2.10 gm (0.03 mol) of potassium methylate in 40 ml of methanol, whereby a clear solution was obtained. Then, 4.38 gm of 6-(2,3-epoxy-propoxy)-3,4-dihydro-carbostyril (m.p. 125°–128° C.) were added while stirring, which also dissolved, accompanied by slight generation of heat. After 5 minutes the separation of a white crystal slurry started. After standing overnight, the crystals were suction-filtered off and recrystallized from a little methanol. White crystals with a melting point of 148°–149° C. were obtained.
Yield: 73% of theory.

EXAMPLE 60

6-(2-Hydroxy-3-phenylsulfinyl-propoxy)-3,4-dihydro-carbostyril

Prepared analogous to Example 2 from 6-(2-hydroxy-3-phenyl-mercapto-propoxy)-3,4-dihydro-carbostyril and hydrogen peroxide.
M.p.: 185°–187° C.
Yield: 51% of theory.

EXAMPLE 61

6-(2-Hydroxy-3-phenylsulfonyl-propoxy)-3,4-dihydro-carbostyril

Prepared analogous to Example 3 from 6-(2-hydroxy-3-phenyl-mercapto-propoxy)-3,4-dihydro-carbostyril and hydrogen peroxide.
M.p.: 170°–172° C.
Yield: 54% of theory.

EXAMPLE 62

7-(4-Phenylmercapto-butoxy)-3,4-dihydro-carbostyril

Prepared analogous to Example 4 from 7-hydroxy-3,4-dihydro-carbostyril (see N. Shigematsu et al., Chem. Pharm. Bull. 1961, 970–975) and 4-phenylmercapto-butyl bromide (bp. 96° to 103° C. at 0.02 mm Hg).
M.p.: 121°–123° C.
Yield: 72% of theory.

EXAMPLE 63

7-(4-Phenylsulfinyl-butoxy)-3,4-dihydro-carbostyril

Prepared analogous to Example 4 from 7-hydroxy-3,4-dihydro-carbostyril (see N. Shigematsu et al., Chem. Pharm. Bull. 1961, 970–975) and 4-phenylsulfinyl-butyl bromide.
M.p.: 134°–136° C.
Yield: 80% of theory.

EXAMPLE 64

7-(4-Phenylsulfonyl-butoxy)-3,4-dihydro-carbostyril

Prepared analogous to Example 4 from 7-hydroxy-3,4-dihydro-carbostyril (see N. Shigematsu et al., Chem. Pharm. Bull. 1961, 970–975) and 4-phenylsulfonyl-butyl bromide.
M.p.: 178.5°–179.5° C.
Yield: 74% of theory.

EXAMPLE 65

8-(4-Phenylmercapto-butoxy)-3,4-dihydro-carbostyril

Prepared analogous to Example 4 from 8-hydroxy-3,4-dihydro-carbostyril (see J. D. Loudon et al., J. Chem. Soc. 1955, 743–744) and 4-phenylmercapto-butyl bromide (bp. 96°–103° C. at 0.02 mm Hg).
M.p.: 101°–102° C.
Yield: 75% of theory.

EXAMPLE 66

8-(4-Phenylsulfinyl-butoxy)-3,4-dihydro-carbostyril

Prepared analogous to Example 4 from 8-hydroxy-3,4-dihydro-carbostyril (see J. D. Loudon et al. in J. Chem. Soc. 1955, 743–744) and phenylsulfinyl-butyl bromide.
Colorless resin.
Yield: 60% of theory.
$R_f$-value: 0.60 (thinlayer chromatogram on slica gel—eluant: benzene/ethanol/conc. ammonia=75/25/1).

EXAMPLE 67

8-(4-Phenylsulfonyl-butoxy)-3,4-dihydro-carbostyril

Prepared analogous to Example 3 from 8-(4-phenylmercapto-butoxy)-3,4-dihydro-carbostyril and hydrogen peroxide.
M.p. 114.5°–115° C.
Yield: 60% of theory.

EXAMPLE 68

6-[4-(2-Benzthiazolyl-sulfonyl)-butoxy]-3,4-carbostyril

Prepared analogous to Example 2 from 6-[4-(2-benzthiazolyl-mercapto)-butoxy]-3,4-dihydro-carbostyril and hydrogen peroxide.
M.p.: 146°–149°.
Yield: 61% of theory.

EXAMPLE 69

6-[4-(2-Quinolyl-mercapto)-butoxy]-3,4-dihydro-carbostyril

Prepared analogous to Example 1 from 6-(4-bromobutoxy)-3,4-dihydro-carbostyril (m.p. 142°–147° C.) and 2-mercapto-quinoline.
M.p.: 115° C.
Yield: 64% of theory.

EXAMPLE 70

6-[4-(2-Quinazolin-4-one-yl-mercapto)-butoxy]-3,4-dihydrocarbostyril

Prepared analogous to Example 1 from 6-(4-bromobutoxy)-3,4-dihydro-carbostyril m.p. 142°–147° C.) and 2-mercaptoquinazoline-4-one.
M.p.: 184.5°–188° C.
Yield: 63% of theory.

EXAMPLE 71

6-[4-(Triphenyl-methyl-mercapto)-butoxy]-3,4-dihydro-carbostyril

Prepared analogous to Example 1 from 6-(4-bromobutoxy)-3,4-dihydro-carbostyril (m.p. 142°–147° C.) and triphenylmethyl-mercaptan.
M.p.: 169°–170° C.
Yield: 89% of theory.

EXAMPLE 72

6-[2-(2-Naphthyl-mercapto)-ethoxy]-3,4-dihydro-carbostyril

Prepared analogous to Example 1 from 6-(4-chlorobutoxy)-3,4-dihydro-carbostyril (m.p.: 147°–148° C.) and 2-naphthyl-mercaptan.
M.p.: 147.5°–147.8° C.
Yield: 77% of theory.

EXAMPLE 73

6-[2-(2-Naphthylsulfinyl)-ethoxy]-3,4-dihydro-carbostyril

Prepared analogous to Example 2 from 6-[2-(2-naphthyl-mercapto)-ethoxy]-3,4-dihydro-carbostyril and hydrogen peroxide.
M.p.: 186.5°–187.5° C.
Yield: 88% of theory.

EXAMPLE 74

6-[2-(4-Bisphenylyl-mercapto)-ethoxy]-3,4-dihydro-carbostyril

Prepared analogous to Example 1 from 6-(2-chloroethoxy)-3,4-dihydro-carbostyril (m.p. 152.5°–153.5° C.) and 4-mercapto-biphenyl.
M.p.: 192°–194° C.
Yield: 92% of theory.

EXAMPLE 75

6-[2-(4-Biphenylyl-sulfinyl)-ethoxy]-3,4-dihydro-carbostyril

Prepared analogous to Example 2 from 6-[2-(4-biphenyl-mercapto)-ethoxy]-3,4-dihydro-carbostyril and hydrogen peroxide.
M.p.: 195°–196° C.
Yield: 66% of theory.

EXAMPLE 76

6-[3-(2-Pyridyl-mercapto)-propoxy]-3,4-dihydro-carbostyril

Prepared analogous to Example 1 from 6-(3-bromopropoxy)-3,4-dihydro-carbostyril and 2-mercapto-pyridine.
M.p.: 108°–108.5° C.
Yield: 42% of theory.

EXAMPLE 77

6-(4-Phenylsulfinyl-butoxy)-3,4-dihydro-carbostyril 1.6 gm of 6-(4-phenylmercapto-butoxy)-3,4-dihydro-carbostyril were dissolved in 50 ml of methanol, and 0.9 gm of N-bromosuccininimide were added. After stirring for 15 hours at room temperature, the mixture was diluted with 500 ml of hot water (80° C.) and decanted from the initially oily precipitate which gradually crystallized. After recrystallization from xylene, white crystals with a melting point of 144° to 145° C. were obtained.

Yield: 1.2 gm (66% of theory).

EXAMPLE 78

6-(4-Phenylsulfinyl-butoxy)-3,4-dihydro-carbostyril 3.3 gm of 6-(4-phenylmercapto-butoxy)-3,4-dihydro-carbostyril were dissolved in 50 ml of methylene chloride, the solution cooled to −70° C., and a solution of 1.5 gm of sulfuryl chloride in 5 ml of methylene chloride was added dropwise. After 15 hours, 20 ml of 95% ethanol were added, and the mixture was heated to room temperature by removing the cooling bath, neutralized with an aqueous sodium carbonate solution. The methylene chloride phase was dried with sodium sulfate, and the solvent was evaporated. The residue was recrystallized from toluene.

M.p.: 143°–145° C.
Yield: 2.8 gm (81% of theory).

EXAMPLE 79

5-(4-Phenylmercapto-butoxy)-3,4-dihydro-carbostyril

Prepared analogous to Example 4 from 5-hydroxy-3,4-dihydro-carbostyril and 4-phenylmercapto-butyl bromide.

M.p.: 155°–157° C.
Yield: 64% of theory.

EXAMPLE 80

5-(4-Phenylsulfinyl-butoxy)-3,4-dihydro-carbostyril

Prepared analogous to Example 4 from 5-hydroxy-3,4-dihydro-carbostyril and 4-phenylsulfinyl-butyl bromide.

M.p.: 136°–138° C.
Yield: 64% of theory.

EXAMPLE 81

5-(4-Phenylsulfonyl-butoxy)-3,4-dihydro-carbostyril

Prepared analogous to Example 4 from 5-hydroxy-3,4-dihydro-carbostyril and 4-phenylsulfonyl-butyl bromide.

M.p.: 187°–189° C.
Yield: 73% of theory.

EXAMPLE 82

6-[4-(2-Naphthyl-sulfonyl)-butoxy]-3,4-dihydro-carbostyril

Prepared analogous to Example 3 from 6-[4-(2-naphthyl-mercapto)-butoxy]-3,4-dihydro-carbostyril and hydrogen peroxide.

M.p.: 173°–175° C.
Yield: 95% of theory.

EXAMPLE 83

6-[4-(4-Biphenylyl-sulfonyl)-butoxy]-3,4-dihydro-carbostyril

Prepared analogous to Example 3 from 6-[4-(4-biphenyl-yl-mercapto)-butoxy]-3,4-dihydro-carbostyril and hydrogen peroxide.

M.p.: 232°–234.5°
Yield: 83% of theory.

EXAMPLE 84

6-(4-Phenylsulfonyl-butoxy)-3,4-dihydro-carbostyril

Prepared analogous to Example 3 from 6-(4-phenylsulfinyl-butoxy)-3,4-dihydro-carbostyril and hydrogen peroxide.

M.p.: 157°–158° C.
Yield: 88% of theory.

EXAMPLE 85

6-[4-(2-Pyridyl-sulfonyl)-butoxy]-3,4-dihydro-carbostyril

Prepared analogous to Example 3 from 6-[4-(2-pyridyl-sulfinyl)-butoxy]-3,4-dihydro-carbostyril and hydrogen peroxide.

M.p.: 123.8°–125° C.
Yield: 76% of theory.

EXAMPLE 86

5-(4-Phenylsulfonyl-butoxy)-carbostyril 1.87 gm of 2,3-dichloro-5,6-dicyano-benzoquinone were added to a solution of 1.8 gm of 5-(4-phenylsulfonyl-butoxy)-3,4-dihydro-carbostyril in 45 ml of dioxane, and the solution was boiled for 2.5 hours on an oil bath. The reaction mixture was then filtered while still hot, and the insoluble matter, which was formed during the reaction was washed with hot dioxane. The combined filtrates were diluted with 100 ml of chloroform and extracted several times with altogether 150 ml of 2N sodium hydroxide. After drying the chloroform extracts with sodium sulfate and filtering in the presence of activated charcoal, the filtrate was concentrated by evaporation, and ethyl acetate was added until white crystals were precipitated.

M.p.: 182°–183° C.
Yield: 850 mgm (47% of theory).

EXAMPLE 87

5-(4-Phenylmercapto-butoxy)-carbostyril

Prepared analogous to Example 86 from 5-(4-phenylmercapto-butoxy)-3,4-dihydro-carbostyril and 2,3-dichloro-5,6-dicyano-benzoquinone.

M.p.: 185°–187° C.
Yield: 40% of theory.

EXAMPLE 88

5-(4-Phenylsulfinyl-butoxy)-carbostyril 0.165 ml of 30% hydrogen peroxide, dissolved in 8 ml of glacial acetic acid, were added to 0.56 gm of 5-(4-phenylmercapto-butoxy)-carbostyril. The mixture was diluted with water and extracted twice with chloroform. The chloroform extract was washed with dilute sodium carbonate solution and with water, dried over magnesium sulfate and evaporated. The residue was admixed with ethyl acetate, yielding colorless crystals with a melting point of 155°–157° C.

Yield: 389 mgm (65% of theory).

EXAMPLE 89

6-(4-Phenylmercapto-butoxy)-carbostyril

Prepared analogous to Example 86 from 6-(4-phenyl-mercapto-butoxy)-3,4-dihydro-carbostyril and 2,3-dichloro-4,5-dicyano-benzoquinone.
M.p.: 162°–164° C.
Yield: 35% of theory.

EXAMPLE 90

6-(4-Phenylsulfinyl-butoxy-carbostyril

Prepared analogous to Example 86 from 6-(4-phenyl-sulfinyl-butoxy)-3,4-dihydrocarbostyril and 2,3-dichloro-5,6-dicyano-benzoquinone. For purification the mixture was chromatographed on a silica gel column with a mixture of benzene/ethanol/conc. ammonia=75/25/3.
M.p.: 181°–182.5° C.
Yield: 48% of theory.
From the first fractions of the column chromatography 6-(4-phenylmercapto-butoxy)-carbostyril, m.p. 162°–164° C., was isolated with a yield of 15% of theory.

EXAMPLE 91

6-(4-Phenylsulfonyl-butoxy)-carbostyril

Prepared analogous to Example 86 from 6-(4-phenyl-sulfonyl-butoxy)-3,4-dihydro-carbostyril and 2,3-dichloro-5,6-dicyano-benzoquinone. Purification was carried out by column chromatography on silica gel (particle size: 0.2–0.5 mm) with chloroform/methanol/ethyl acetate=4/1/1.
M.p.: 212°–213° C.
Yield: 54% of theory.

EXAMPLE 92

5-(4-Phenylmercapto-butoxy)-carbostyril 49 gm of 4-phenylmercapto-butyl bromide were added to a mixture of 32.3 gm of 5-hydroxy-carbostyril, 30 gm of potassium carbonate and 650 ml of dimethylsulfoxide which had been dried over a molecular sieve. The mixture was stirred for 20 hours at 25° C., diluted with 3 liters of water, and the crystallized reaction product was suction-filtered off.
M.p.: 185°–187° C. (from toluene)
Yield: 45.0 gm (70% of theory).

EXAMPLE 93

5-(4-Phenylsulfonyl-butoxy)-carbostyril

Prepared analogous to Example 88 from 5-(4-phenyl-mercapto-butoxy-carbostyril and 4 mols of hydrogen peroxide at a temperature of 60° C., with a reaction time of 14 hours.
M.p.: 182°–183° C.
Yield: 73% of theory.

EXAMPLE 94

6-(4-Phenylmercapto-butoxy)-carbostyril

Prepared analogous to Example 92 from 6-hydroxy-carbostyril and 4-phenylmercapto-butyl bromide.
M.p.: 161°–163° C.
Yield: 78% of theory.

EXAMPLE 95

6-(4-Phenylsulfinyl-butoxy)-carbostyril

Prepared analogous to Example 88 from 6-(4-phenyl-mercapto-butoxy)-carbostyril and hydrogen peroxide.
M.p.: 181°–182° C.
Yield: 68% of theory.

EXAMPLE 96

6-(4-Phenylsulfinyl butoxy)-carbostyril

Prepared analogous to Example 92 from 6-hydroxy-carbostyril and 4-phenylsulfinyl-butyl bromide.
M.p.: 181°–182° C.
Yield: 71% of theory.

EXAMPLE 97

7-(4-Phenylsulfinyl-butoxy)-carbostyril

Prepared analogous to Example 86 from 7-(4-phenyl-sulfinyl-butoxy)-3,4-dihydro-carbostyril.
M.p.: 193°–194° C.
Yield: 51% of theory.

EXAMPLE 98

8-(4-Phenylmercapto-butoxy)-carbostyril

Prepared analogous to Example 86 from 8-(4-phenyl-mercapto-butoxy)-3,4-dihydro-carbostyril and 2,3-dichloro-5,6-dicyano-benzoquinone.
M.p.: 119°–120° C.
Yield: 40% of theory.

EXAMPLE 99

8-(4-Phenylsulfinyl-butoxy)-carbostyril

Prepared analogous to Example 88 from 8-(4-phenyl-mercapto-butoxy)-carbostyril by oxidation with hydrogen peroxide.
M.p.: 125.5°–126.5° C.
Yield: 60% of theory.

EXAMPLE 100

5-(4-Phenylsulfonyl-butoxy)-carbostyril 100 mgm of 5-(4-phenylsulfonyl-butoxy)-3,4-dihydro-carbostyril were refluxed with 30 mgm of palladium-on-charcoal and 1 ml of mesitylene. After 3.5 hours, another 30 mgm of palladium-on-charcoal were added, and the mixture was heated for 9 hours more. Subsequently, the reaction mixture was filtered while still hot, the filtrate was evaporated, and the residue was chromatographed on a silica gel column with a mixture of benzene/ethanol/conc. ammonia=75/25/3. Besides unreacted starting material, 9 mgm of 5-(4-phenylsulfo-nyl-butoxy)-carbostyril were obtained.
M.p.: 182°–183° C.

EXAMPLE 101

6-(4-(Amino-iminomethylmercapto-butoxy)-3,4-dihydro-carbostyril

A mixture of 18 gm of 6-(4-bromo-butoxy)-3,4-dihydro-carbostyril, 5 gm of thiourea and 250 ml of water was boiled until a solution was obtained (about 4 hours). After cooling, the impurities were extracted with chloroform and the aqueous phase was made alkaline with ammonia. The precipitated crystals were suction-filtered off and dried.
M.p.: 140°–141.8° C.
M.p. of the hydrochloride: 208°–211° C.

EXAMPLE 102

6-(4-Phenylsulfonyl-butoxy)-3,4-dihydro-carbostyril 107 mgm of 6-(4-phenylsulfonyl-butoxy)-carbostyril were suspended in 15 ml of methanol, the suspension was admixed with 40 mgm of palladium-on-charcoal, and the mixture was hydrogenated at 50° C. and a hydrogen pressure of 2.5 bar for 14 hours. After filtering off the catalyst and evaporating the clear solution, a colorless crystalline residue was obtained.

M.p.: 153°–154° C.
Yield: 89 mgm (83% of theory).

EXAMPLE 103

6-(4-Benzylmercapto-butoxy)-3,4-dihydro-carbostyril

A solution of 2.5 gm of 6-(4-mercapto-butoxy)-3,4-dihydro-carbostyril in 25 ml of dimethysulfoxide was mixed whilst stirring with 1.4 gm of potassium carbonate and subsequently with 1.3 ml of benzyl chloride. After stirring for 15 hours at room temperature, the reaction mixture was diluted with 200 ml of water, and the precipitated oily substance was separated and recrystallized from ethyl acetate.

M.p.: 76°–78° C.
Yield: 2.8 gm (82% of theory).

EXAMPLE 104

6-(5-Phenylmercapto-pentoxy)-3,4-dihydro-carbostyril

Prepared analogous to Example 1 from 6-(5-bromopentoxy)-3,4-dihydro-carbostyril and thiophenol.

M.p.: 117°–119° C.
Yield: 71% of theory.

EXAMPLE 105

6-(5-Phenylsulfinyl-pentoxy)-3,4-dihydro-carbostyril

Prepared analogous to Example 2 from 6-(5-phenylmercapto-pentoxy)-3,4-dihydro-carbostyril and hydrogen peroxide.

M.p.: 104°–109.5° C.
Yield: 66% of theory.

EXAMPLE 106

6-(5-Phenylsulfonyl-pentoxy)-3,4-dihydro-carbostyril

Prepared analogous to Example 3 from 6-(5-phenylmercapto-pentoxy)-3,4-dihydro-carbostyril and hydrogen peroxide.

M.p.: 136.5°–137.8° C.
Yield: 62% of theory.

EXAMPLE 107

6-[5-(2-Pyridyl-mercapto)-pentoxy]-3,4-dihydro-carbostyril

Prepared analogous to Example 1 from 6-(5-bromopentoxy)-3,4-dihydro-carbostyril and 2-mercapto-pyridine.

M.p.: 113°–114.8° C.
Yield: 76% of theory.

EXAMPLE 108

5-(2-Hydroxy-3-phenylmercapto-propoxy)-3,4-dihydro-carbostyril

Prepared analogous to Example 59 from 5-(2,3-epoxy-propoxy)-3,4-dihydro-carbostyril and thiophenol.

M.p.: 135°–137° C.
Yield: 64% of theory.

EXAMPLE 109

5-(2-Hydroxy-3-phenylsulfinyl-propoxy)-3,4-dihydro-carbostyril

Prepared analogous to Example 2 from 5-(2-hydroxy-3-phenylmercapto-propoxy)-3,4-dihydro-carbostyril and hydrogen peroxide.

M.p.: 186°–188° C.
Yield: 60% of theory.

EXAMPLE 110

5-(2-Hydroxy-3-phenylsulfonyl-propoxy)-3,4-dihydro-carbostyril

Prepared analogous to Example 3 from 5-(2-hydroxy-3-phenyl-mercapto-propoxy)-3,4-dihydro-carbostyril and hydrogen peroxide.

M.p.: 168°–170° C.
Yield: 53% of theory.

EXAMPLE 111

6-[4-(4-Hydroxyphenyl-mercapto)-butoxy]-3,4-dihydro-carbostyril

Prepared analogous to Example 1 from 6-(4-bromo-butoxy)-3,4-dihydro-carbostyril and 4-hydroxy-thiophenol.

M.p.: 191.5°–193.0° C.
Yield: 83% of theory.

EXAMPLE 112

6-[4-(4-Hydroxyphenyl-sulfinyl)-butoxy]-3,4-dihydro-carbostyril

Prepared analogous to Example 2 from 6-[4-(4-hydroxy-phenyl-mercapto)-butoxy]-3,4-dihydro-carbostyril and hydrogen peroxide.

M.p.: 206°–207.8° C.
Yield: 84% of theory.

EXAMPLE 113

6-[4-(4-Hydroxyphenyl-sulfonyl)-butoxy]-3,4-dihydro-carbostryil

Prepared analogous to Example 3 from 6-[4-(4-hydroxy-phenyl-mercapto)-butoxy]-3,4-dihydro-carbostyril and hydrogen peroxide.

M.p.: 219°–219.5° C.
Yield: 78% of theory.

EXAMPLE 114

6-[4-(4-Acetaminophenyl-mercapto)-butoxy]-3,4-dihydro-carbostyril

Prepared analogous to Example 1 from 6-(4-bromo-butoxy)-3,4-dihydro-carbostyril and 4-acetamino-thiophenol.

M.p.: 162.5°–163.0° C.
Yield: 65% of theory.

EXAMPLE 115

6-[4-(4-Acetaminophenyl-sulfinyl)-butoxy]-3,4-dihydro-carbostyril

Prepared analogous to Example 2 from 6-[4-(4-acetaminophenyl-mercapto)-butoxy]-3,4-dihydro-carbostyril and hydrogen peroxide.

M.p.: 202.0°–203.8° C.
Yield: 55% of theory.

EXAMPLE 116

6-[4-(4-Acetaminophenyl-sulfonyl)-butoxy]-3,4-dihydro-carbostyril

Prepared analogous to Example 3 from 6-[4-(4-acetaminophenyl-mercapto)-butoxy]-3,4-dihydro-carbostyril and hydrogen peroxide.
M.p.: 143.5°–147.0° C.
Yield: 88% of theory.

EXAMPLE 117

6-[4-(4,5-Di-p-chlorophenyl-oxazol-2-yl-mercapto)-butoxy]-3,4-dihydro-carbostyril Prepared analogous to Example 1 from 6-(4-bromo-butoxy)-3,4-dihydro-carbostyril and 2-mercapto-4,5-di-p-chlorophenyl-oxazole.
M.p.: 110°–115° C.
Yield: 70% of theory.

EXAMPLE 118

6-[4-(2-Pyridyl-sulfinyl)-butoxy]-carbostyril

Prepared analogous to Example 86 from 6:[4-(2-pyridyl-sulfinyl)-butoxy]-3,4-dihydro-carbostyril and 2,3-dichloro-5,6-dicyano-benzoquinone.
M.p.: 152°–154° C.
Yield: 48% of theory.

EXAMPLE 119

6-(4-Phenylmercapto-butoxy)-3,4-dihydro-carbostyril

Prepared analogous to Example 102 from 6-(4-phenyl-mercapto-butoxy)-carbostyril by catalytic hydrogenation with rhenium-VII-sulfide as catalyst.
M.p.: 121°–122° C.
Yield: 67% of theory.

EXAMPLE 120

8-(4-Phenylsulfonyl-butoxy)-carbostyril

Prepared analogous to Example 86 from 8-(4-phenylsulfonyl-butoxy)-3,4-dihydro-carbostyril and 2,3-dichloro-5,6-dicyano-benzoquinone.
M.p.: 146°–147° C.
Yield: 41% of theory.

EXAMPLE 121

7-(4-Phenylmercapto-butoxy)-carbostyril

Prepared analogous to Example 86 from 7-(4-phenyl-mercapto-butoxy)-3,4-dihydro-carbostyril and 2,3-dichloro-5,6-dicyano-benzoquinone.
M.p.: 157.5°–158.5° C.
Yield: 54% of theory.

EXAMPLE 122

6-[4-(2,5-Dichlorophenyl-mercapto)-butoxy]-3,4-dihydro-carbostyril 8.94 gm (0.03 mol) of 6-(4-bromo-butoxy)-3,4-dihydro-carbostyril (m.p. 142°–147° C.) were added to a solution of 2.21 gm (0.0315 mol) of potassium methylate and 5.76 gm (0.0315mol) of 98% 2,5-dichloro-thiophenol in 54 ml of methanol. The mixture was refluxed, whereupon at first a clear solution was obtained. After 5 minutes so much crystalline reaction product was separated out that the reaction mixture solidified into a barely stirrable crystal slurry. After one hour the mixture was cooled to room temperature, suction-filtered and the filter cake was recrystallized from ethanol. Colorless crystals with a melting point of 133°–134° C. were obtained.
Yield: 10.60 gm (89.1% of theory).

EXAMPLE 123

6-[4-(2,5-Dichlorophenylsulfinyl)-butoxy]-3,4-dihydro-carbostyril

A suspension of 5.55 gm (0.014 mol) of 6-[4-(2,5-dichlorophenyl-mercapto)-butoxy]-3,4-dihydro-carbostyril in 40 ml of glacial acetic acid was admixed with 1.19 ml of an aqueous 40.06% solution of hydrogen peroxide (0.014 mol) dissolved in 1.5 ml of glacial acetic acid, and the mixture was stirred at room temperature. The suspension cleared, and an almost clear solution was obtained. After 70 hours white crystals separated out, which were suction-filtered off and recrystallized from ethanol.
M.p.: 185°–186° C.
Yield: 5.43 gm (94.1% of theory).

EXAMPLE 124

6-[4-(2,5-Dichlorophenyl-sulfonyl)-butoxy]-3,4-dihydro-carbostyril 2.97 gm (0.0075 mol) of 6-[4-(2,5-dichlorophenyl-mercapto)-butoxy]-3,4-dihydro-carbostyril were introduced into 15 ml of ice cold formic acid, and the mixture was combined with 1.49 ml of 40.08% hydrogen peroxide. (0.0175 mol). After stirring for 2.5 hours, the mixture was diluted with three times the amount of water. The precipitated crystals were recrystallized from ethanol.
M.p.: 174.5°–175.5° C.
Yield: 1.99 gm (61.9% of theory).

EXAMPLE 125

6-[4-(3,4-Dichlorophenyl-sulfonyl)-butoxy]-3,4dihydro-carbostyril

Prepared analogous to Example 124 from 6-[4-(3,4-dichlorophenyl-mercapto)-butoxy]-3,4-dihydro-carbostyril (m.p. 116.5°–118° C.) and hydrogen peroxide.
M.p.: 172°–173° C.
Yield: 96% of theory.

EXAMPLE 126

6-[4-(4-Hydroxy-3,5di-tert. butylphenyl-mercapto)-butoxy]-3,4-dihydro-carbostyril Prepared analogous to Example 122 from 6-(b 4-bromo-butoxy)-3,4-dihydro-carbostyril (m.p. 142°–147° C.) and 4-hydroxy-3,5-di-tert. butyl-thiophenol.
M.p.: 146°–147° C.
Yield: 68.8% of theory.

EXAMPLE 127

6-[4(4-Hydroxy-3,5-di-tert. butylphenyl-sulfinyl)-butoxy]-3,4-dihydro-carbostyril Prepared analogous to Example 123 from 6-[4-(4-hydroxy-3,5di-tert. butyphenyl-mercapto)-butoxy]-3,4-dihydro-carbostyril and hydrogen peroxide.
M.p.: 170°–171° C.
Yield: 80.7% of theory.

EXAMPLE 128

6-[4-(4-Hydroxy-3,5-di-tert. butylphenyl-sulfonyl)-butoxy]-3,4-dihydro-carbostyril Prepared analogous to Example 124 from 6-[4-(4-hydroxy- 3,5-di-tert. butylphenyl-mercapto)-butoxy]-3,4-dihyldro-carbostyril and hydrogen peroxide.
M.p.: 165°–167° C.
Yield: 97.6 of theory.

EXAMPLE 129

6-[4-(2-Carboxyphenyl-mercapto)-butoxy]-3,4-dihydro-carbostyril

Prepared analogous to Example 122 from 6-(4-bromo-butoxy)-3,4-dihydro-carbostyril and 2-thiobenzoic acid.
M.p.: 176°–179° C.
Yield: 57.5% of theory.

EXAMPLE 130

6-[4-(2-Carboxyphenyl-sulfinyl)-butoxy]-3,4-dihydro-carbostyril

Prepared analogous to Example 123 from 6-[4-(2-carboxyphenyl-mercapto)-butoxy]-3,4-dihydro-carbostyril and hydrogen peroxide. M.p.: 194°–196° C. Yield: 77.2% of theory.

EXAMPLE 131

6-[4-(4-Pyridyl-sulfinyl)-butoxy]-3,4-dihydro-carbostyril

Prepared analogous to Example 122 from 6-(4-bromo-butoxy)-3,4-dihydro-carbostyril and 4-mercapto-pyridine and subsequent oxidation of the intermediate 6-[4-(4-pyridyl-mercapto)-butoxy]-3,4-dihydro-carbostyril (m.p. 128°–133° C.) with hydrogen peroxide analogous to Example 123.
M.p.: 154° C.
Yield: 57% of theory.

EXAMPLE 132

6-[4-(4-Pyridiyl-sulfonyl)-butoxy]-3,4dihydro-carbostyril

Prepared analogous to Example 124 from 6-[4-(4-pyridylmercapto)-butoxy]-3,4-dihydro-carbostyril and hydrogen peroxide.
M.p.: 179°–183° C.
Yield: 35.9% of theory.

EXAMPLE 133

6-[3-(3,4-Dichlorophenyl-sulfinyl)-2-hydroxy-propoxy]-3,4-dihydro-carbostyril

A solution of 3.51 gm (0.016 mol) of 6-(2,3-epoxy-propoxy)-3,4-dihydro-carbostyril (m.p. 125°–128° C.) in 35 ml of methanol was admixed with 4.29 gm of 3,4-dichlorothiophenol, and the mixture was boiled for 5 hours. After cooling, crystals were obtained which were suction-filtered off and recrystallized from ethanol.
M.p.: 175°–176° C.
Yield: 2.48 gm (38.9% of theory).

The 6-[3-(3,4-dichlorophenyl-mercapto)-2-hydroxy-propoxy]-3,4-dihydro-carbostyril thus obtained, was oxidized analogous to Example 123 with hydrogen peroxide.
M.p.: 108°–110° C.
Yield: 75% of theory.

EXAMPLE 134

6-(3-Benzylmercapto-propoxy)-3,4-dihydro-carbostyril

Prepared analogous to Example 122 from 6-(3-bromo-propoxy)-3,4-dihydro-carbostyril (m.p.: 142°–147° C.) and benzyl-mercaptan.
M.p.: 97.5°–99.0° C.
Yield: 58% of theory.

EXAMPLE 135

6-(3-Benzylsulfinyl-propoxy)-3,4-dihydro-carbostyril

Prepared analogous to Example 123 from 6-(3-benzylmercapto-propoxy)-3,4-dihydro-carbostyril and hydrogen peroxide.
M.p.: 144.5°–147.0° C.
Yield: 51% of theory.

EXAMPLE 136

5-(3-tert. Butylmercapto-2-hydroxy-propoxy)-3,4-dihydro-carbostyril

Prepared analogous to Example 133 from 5-(2,3-epoxy-propoxy)-3,4-dihydro-carbostyril (m.p. 171°–173° C.) and tert. butyl mercaptan.
M.p.: 105°–109° C.
Yield: 77.1% of theory.

EXAMPLE 137

5-(3-tert. Butylsulfinyl-2-hydroxy-propoxy)-3,4-dihydro-carbostyril.

Prepared analogous to Example 123 from 6-(3-tert. butylmercapto-2-hydroxy-propoxy)-3,4-dihydro-carbostyril and hydrogen peroxide.
M.p.: 175°–177° C.
Yield: 52.1% of theory.

EXAMPLE 138

5-(3-tert. Butylsulfonyl-2-hydroxy-propoxy)-3,4-dihydro-carbostyril

Prepared analogous to Example 124 from 6-(3-tert. butylmercapto-2-hydroxy-propoxy)-3,4-dihydro-carbostyril and hydrogen peroxide.
M.p.: 210°–212° C.
Yield: 37.1% of theory.

EXAMPLE 139

6-[4-(2-Pyridyl-sulfonyl)-butoxy]-carbostyril

Prepared analogous to Example 124 from 6-[4-(2-pyridylsulfinyl)-butoxy]-carbostyril and hydrogen peroxide.
M.p.: 179°–180° C.
Yield: 65.8% of theory.

EXAMPLE 140

4-Methyl-6-(4-phenylmercapto-butoxy)-carbostyril

A mixture of 5.25 gm (0.03 mol) of 4-methyl-6-hydrocarbostyril [m.p. 326°–330° C.; see R. R. Holmes et al., J. Amer. Chem. Soc. 76, 2404 (1954)], 8.09 gm (0.033 mol) of 4-phenylmercapto-butyl bromide, 6.22 gm (0.045 mol) of potassium carbonate and 70 ml dimethylsulfoxide was stirred at room temperature for 16 hours, the mixture was diluted with water, and the precipitated crystals were collected, dried and recrystallized from toluene.

M.p.: 148°–150° C.
Yield: 6.2 gm (61.2% of theory).

EXAMPLE 141

4-Methyl-6-(4-phenylsulfinyl-butoxy)-carbostyril

Prepared analogous to Example 140 from 4-methyl-6-hydroxy-carbostyril (m.p. 326°–330° C.) and 4-phenyl-sulfinyl-butyl bromide.

M.p.: 167°–168° C.
Yield: 47.3% of theory.

EXAMPLE 142

4-Methyl-6-(4-phenylsulfonyl-butoxy)-carbostyril

Prepared analogous to Example 140 from 4-methyl-6-hydroxy-carbostyril (m.p. 326°–330° C.) and 4-phenyl-sulfonyl-butyl-bromide.

M.p.: 217°–219° C.
Yield: 66.6% of theory.

EXAMPLE 143

4-Methyl-6-[4-(2-pyridyl-mercapto)-butoxy]-carbostyril

Prepared analogous to Example 122 from 4-methyl-6-(4-bromo-butoxy)-carbostyril (m.p. 217°–219° C.) and 2-mercapto-pyridine.

M.p.: 149°–151° C.
Yield: 85.7% of theory.

EXAMPLE 144

4-Methyl-6-[4-(2-pyridyl-sulfinyl)-butoxy]-carbostyril

Prepared analogous to Example 123 from 4-methyl-6-[4-(2-pyridyl-mercapto)-butoxy]-carbostyril and hydrogen peroxide.

M.p.: 167°–169° C.
Yield: 61.8% of theory.

EXAMPLE 145

4-Methyl-6-[4-(2-pyridyl-sulfonyl)-butoxy]-carbostyril

Prepared analogous to Example 124 from 4-methyl-6-[4-(2-pyridyl-mercapto)-butoxy]-carbostyril and hydrogen peroxide.

M.p.: 195°–197° C.
Yield: 29.5% of theory.

EXAMPLE 146

4-Methyl-6-[4-(2-quinolyl-mercapto)-butoxy]-carbostyril

Prepared analogous to Example 122 from 4-methyl-6-(4-bromo-butoxy)-carbostyril and 2-mercapto-quinoline.

M.p.: 162°–163° C.
Yield: 81.9% of theory.

EXAMPLE 147

4-Methyl-6-[4-(2-quinolylsulfinyl)-butoxy]-carbostyril

Prepared analogous to Example 123 from 4-methyl-6-[4-(2-quinolyl-mercapto)-butoxy]-carbostyril and hydrogen peroxide.

M.p.: 189°–190° C.
Yield: 47.5% of theory.

EXAMPLE 148

4-Methyl-6-[4-(2-quinolylsulfonyl)-butoxy]-carbostyril

Prepared analogous to Example 124 from 4-methyl-6-[4-(2-quinolyl-mercapto)-butoxy]-carbostyril and hydrogen peroxide.

M.p.: 199°–203° C.
Yield: 31.5% of theory.

EXAMPLE 149

4-Methyl-6-[4-(4-biphenylyl-sulfinyl)-butoxy]-carbostyril

Prepared analogous to Example 123 from 4-methyl-6-[4-(4-biphenylyl-mercapto)-butoxy]-carbostyril (m.p. 174°–176° C.) and hydrogen peroxide.

M.p. 161°–162° C.
Yield: 59% of theory.

EXAMPLE 150

6-[4-(4-Chlorophenyl-mercapto)-butoxy]-carbostyril

Prepared analogous to Example 122 from 6-(4-chlorobutoxy)-carbostyril (m.p. 206°–208° C.) and 4-chlorothiophenol.

M.p.: 168°–170° C.
Yield: 85% of theory.

EXAMPLE 151

6-[4-(4-Chlorophenyl-sulfinyl)-butoxy]-carbostyril

Prepared analogous to Example 123 from 6-[4-(4-chlorophenyl-mercapto)-butoxy]-carbostyril and hydrogen peroxide.

M.p.: 157°–158° C.
Yield: 81% of theory.

EXAMPLE 152

6-[4-(4-Chlorophenyl-sulfonyl)-butoxy]-carbostyril

Prepared analogous to Example 124 from 6-[4-(4-chlorophenyl-mercapto)-butoxy]-carbostyril and hydrogen peroxide.

M.p.: 197°–199° C.
Yield: 99% of theory.

EXAMPLE 153

6-[4-(3,4-Dichlorophenyl-mercapto)-butoxy]-carbostryil

Prepared analogous to Example 122 from 6-(4-bromobutoxy)-carbostyril (m.p. 198°–199° C.) and 3,4-dichlorothiophenol.

M.p.: 149°–152° C.
Yield: 60% of theory.

EXAMPLE 154

6-[4-(3,4-Dichlorophenyl-sulfinyl)-butoxy]-carbostyril

Prepared analogous to Example 123 from 6-[4-(3,4-dichloro-phenyl-mercapto)-butoxy]-carbostyril and hydrogen peroxide.

M.p.: 191°–196° C.
Yield: 87% of theory.

EXAMPLE 155

6-[4-(3,4-Dichlorophenyl-sulfonyl)-butoxy]-carbostyril

Prepared analogous to Example 124 from 6-[4-(3,4-dichloro-phenyl-mercapto)-butoxy]-carbostyril and hydrogen peroxide.

M.p.: 188°–190° C.
Yield: 83% of theory.

EXAMPLE 156

6-[4-(2,5-Dichlorophenyl)-mercapto)-butoxy]-carbostyril

Prepared analogous to Example 122 from 6-(4-bromobutoxy)-carbostyril and 2,5-dichloro-thiophenol.
M.p.: 175°–176° C.
Yield: 85% of theory.

EXAMPLE 157

6-[4-(2,5-Dichlorophenyl-sulfinyl)-butoxy]-carbostyril

Prepared analogous to Example 123 from 6-[4-(2,5-dichloro-phenyl-mercapto)-butoxy]-carbostyril and hydrogen peroxide.
M.p.: 200°–202° C.
Yield: 75% of theory.

EXAMPLE 158

6-[4-(2,5-Dichlorophenyl-sulfonyl)-butoxy]-carbostyril

Prepared analogous to Example 124 from 6-[4-(2,5-dichloro-phenyl-mercapto)-butoxy]-carbostyril and hydrogen peroxide in formic acid.
M.p.: 203°–205° C.
Yield: 79% of theory.

EXAMPLE 159

6-[4-(4-Fluorophenyl-mercapto)-butoxy]-carbostyril

Prepared analogous to Example 122 from 6-(4-bromobutoxy)-carbostyril and 4-fluoro-thiopyhenol.
M.p.: 149°–150° C.
Yield: 85% of theory.

EXAMPLE 160

6-[4-(4-Fluorophenyl-sulfinyl)-butoxy]-carbostyril

Prepared analogous to Example 123 from 6-[4-(4-fluorophenyl-mercapto)-butoxy]-carbostyril and hydrogen peroxide.
M.p.: 164°–165° C.
Yield: 50% of theory.

EXAMPLE 161

6-[4-(4-Fluorophenyl-sulfonyl)-butoxy]-carbostyril

Prepared analogous to Example 124 from 6-[4-(4-fluorophenyl-mercapto)-butoxy]-carbostyril and hydrogen peroxide in formic acid.
M.p.: 209°–211° C.
Yield: 59% of theory.

EXAMPLE 162

6-[4-(4-Hydroxy-3,5-di-tert. butylphenyl-mercapto)-butoxy]-carbostyril

Prepared analogous to Example 122 from 6-(4-bromobutoxy)-carbostyril (m.p. 198°–199° C.) and 4-hydroxy-3,5-di-tert. butyl-thiophenol (m.p. 84.5°–86.0° C.).
M.p.: 172°–173° C.
Yield: 77% of theory.

EXAMPLE 163

6-[4-(4-Hydroxy,3,5-di-tert. butylphenyl-sulfinyl)butoxy]-carbostyril

Prepared analogous to Example 123 from 6-[4-(4-hydroxy-3,5-di-tert. butylphenyl-mercapto)-butoxy]-carbostyril and hydrogen peroxide.
M.p.: 192°–194° C.
Yield: 83% of theory.

EXAMPLE 164

6-[4-(4-Hydroxy-3,5-di-tert. butylphenyl-sulfonly)-butoxy]-carbostyril

Prepared analogous to Example 124 from 6-[4-(4-hydroxy-3,5-di-tert. butylphenyl-mercapto)-butoxy]-carbostyril and hydrogen peroxide in formic acid.
M.p.: 242°–244° C.
Yield: 92% of theory.

EXAMPLE 165

6[4-(4-Biphenylyl-mercapto)-butoxy]-carbostyril

Prepared analogous to Example 122 from 6-(4-bromo-butoxy)-carbostyril (m.p. 198°–199° C.) and 4-biphenyl-mercaptan.
M.p.: 191°–192° C.
Yield: 82% of theory.

EXAMPLE 166

6-[4-(4-Biphenylyl-sulfinyl)-butoxy]-carbostyril

Prepared analogous to Example 123 from 6-[4-biphenylyl-mercapto)-butoxy]-carbostyril and hydrogen peroxide.
M.p.: 196°–197° C.
Yield: 80% of theory.

EXAMPLE 167

6-[4-(4-Biphenylyl-sulfonyl)-butoxy]-carbostyril

Prepred analogous to Example 124 from 6[4-biphenyl-yl-mercapto)-butoxy]-carbostyril and hydrogen peroxide.
M.p.: 213°–215° C.
Yield: 73% of theory.

EXAMPLE 168

6-[4-(4-Nitrophenyl-mercapto)-butoxy]-carbostyril

Prepared analogous to Example 122 from 6-(4-bromo-butoxy)-carbostryil (m.p. 198°–199° C.) and 4-nitro-thiophenol.
M.p.: 184°–185° C.
Yield: 96% of theory.

EXAMPLE 169

6-[4-(4-Nitrophenyl-sulfinyl)-butoxy]-carbostyril

Prepared analogous to Examples 123 from 6-[4-(4-nitrophenyl-mercapto)-butoxy]-carbostyril and hydrogen peroxide.
M.p.: 183°–184° C.
Yield: 77% of theory.

EXAMPLE 170

6-[4-(4-Nitrophenyl-sulfonyl)-butoxy]-carbostyril

Prepared analogous to Example 124 from 6-[4-(4-nitro-phenyl-sulfinyl)-butoxy]-carbostyril and hydrogen peroxide in formic acid.

M.p.: 230°–232° C.
Yield: 70% of theory.

EXAMPLE 171

6-[4-(2-Quinolyl-mercapto)-butoxy]-carbostyril

Prepared analogous to Example 122 from 6-(4-bromo-butoxy)-carbosytril (m.p.- 132° C.) and 2-mercapto-quinoline.
M.p.: 132° C.
Yield: 99% of theory.

EXAMPLE 172

6-[4-(2-Quinolyl-sulfinyl)-butoxy]-carbostyril

Prepared analogous to Example 123 from 6-[4-(2-quinolyl-mercapto)-butoxy]-carbostyril and hydrogen peroxide.
M.p.: 161°–162° C.
Yield: 66% of theory.

EXAMPLE 173

6-[4-(2-Quinolyl-sulfonyl)-botoxy]-carbostyril

Prepared analogous to Example 124 from 6-[4-(2-quinolyl-sulfinyl)-butoxy]-carbostyril and hydrogen peroxide in formic acid.
M.p.: 197°–198° C.
Yield: 58% of theory.

EXAMPLE 174

5-(4-Phenylmercapto-butoxy)-oxindole

Prepared analogous to Example 140 from 5-hydroxy-oxindole (J. Chem. Soc. 1961, 2723) and 4-phenylmercapto- butyl bromide.
M.p.: 131°–132° C.
Yield: 13% of theory.

EXAMPLE 175

5-(4-Phenylsulfinyl-butoxy)-oxindole

Prepared analogous to Example 123 from 5-(4-phenyl-mercapto-butoxy)-oxindole and hydrogen peroxide.
M.p.: 114°–116° C.
Yield: 61% of theory.

EXAMPLE 176

6-[2-(Phenylsulfinyl-methyl)-benzyloxy]3,4-dihydro-carbo-styril

A mixture of 67.1 gm of phthalide, 51.3 ml of thiophenol, 35.1 gm of potassium methylate and 250 ml of methanol was refluxed. Subsequently, the obtained 2-(phenylmercapto-methyl) -benzoic acid (yield: 78% of theory, m.p. 108°–110° C.) was esterified with methanol/thionylchloride by standing at −40° C. After standing overnight at room temperature, methyl 2-(phenylmercapto-methyl)-benzoate (yield: 89% of theory, b.p. 145° C. at 0.07 mm Hg) was obtained, which was converted into 2-(phenylmercapto-methyl)-phenyl carbinol (yield: 97% of theory, m.p. 64°–65° C.) by reduction with lithium aluminum hydride in diethyl ether.

This compound was reacted with p-toluene sulfonyl chloride into 2-(phenylmercapto-methyl)-phenyl carbinol p-toluenesulfonate. (Thin-layer chromatrogram) silica gel; eluant: chloroform/ethyl acetate = 1:1; R$_f$-value=0.8. Yield: 55% of theory). This ester was reacted analogous to Example 140 with 6-hydroxy-3,4-dihydro-carbosyt-ril to form 6-[2-(phenylmercapto-methyl)-benzyloxy]-3,4-dihydroxcarbostyril (thin-layer chromatogram; silica gel: eluant: chloroform/ethyl acetate = 1:1; R$_f$-value=0.35; Yield: 64% of theory).

This substance was, analogous to Example 123, oxidized into 6-[2-(phenylsulfinyl-methyl)-benzyloxy]-3,4-dihydro-carbostyril with hydrogen peroxide.
M.p.: 133°–135° C.
Yield: 64% of theory.

EXAMPLE 177

6-[4-(Phenylmercapto-methyl)-benzyloxy]-3,4-dihydro-carbostyril p-Xylylene dichloride was reacted with thiophenol in a mol ratio of 1:1 in the presence of excess potassium carbonate in dimethylsulfoxide. The obtained 4-(phenyl-mercapto-methyl)-benzyl chloride (identification: thin-layer chromatogram) was further reacted with 6-hydroxy-3, 4-dihydro-carbostyril analogous to Example 140 without isolation.
M.p.: 139°–141° C.
Yield: 52% of theory.

EXAMPLE 178

6-[4-(phenyl-sulfinyl)-benzyloxy]-3,4-dihydro-carbostyril

Prepared analogous to Example 123 from 6-[4-(phenyl-mercapto -methyl)-benzyloxy]-3,4-dihydro-carbostyril and hydrogen peroxide.
M.p.: 179°–181° C.
Yield: 61% of theory.

EXAMPLE 179

6-(4-Cyclohexylmercapto-butoxy)-carbostyril

Prepared analogous to Example 122 from 6-(4-bromobutoxy)-carbostyril (m.p.: 198°–199° C.) and cyclohexyl mercaptan.
M.p.: 153°–159° C.
Yield: 89% of theory.

EXAMPLE 180

6-(4-Cyclohexylsulfinyl-butoxy)-carbostyril

Prepared analogous to Example 123 from 6-(4-cyclohexylmercapto-butoxy)-carbostyril and hydrogen peroxide.
M.p.: 169°–170° C.
Yield: 57% of theory.

EXAMPLE 181

6-[4-(4-Bromophenyl-mercapto)-butoxy]-carbostyril

Prepared analogous to Example 122 from 6-(4-bromobutoxy)-carbostyril (m.p. 198°–199° C.) and 4-bromo-thiophenol.
M.p.: 156°–158° C.
Yield: 53% of theory.

EXAMPLE 182

6-[4-(4-Bromophenyl-sulfinyl)-butoxy]-carbostyril

Prepared analogous to Example 123 from 6-[4-(4-bromophenyl-mercapto)-butoxy]-carbostyril and hydrogen peroxide.
M.p.: 168°–170° C.
Yield: 65% of theory.

EXAMPLE 183

6-[4-(3-Methyl-4-bromo-phenylmercapto)-butoxy]-carbostyril

Prepared analogous to Example 122 from 6-(4-bromobutoxy)-carbostyril (m.p. 189°–199° C.) and 3-methyl-4-bromo-thiophenol.
M.p.: 167°–169° C.
Yield: 76% of theory.

EXAMPLE 184

6-[4-(3-Methyl-4-bromo-phenylsulfinyl)-butoxy]-carbostyril

Prepared analogous to Example 123 from 6-[4-(3-methyl-4-bromo-phenylmercapto)-butoxy]-carbostyril and hydrogen peroxide.
M.p.: 169°–172° C.
Yield: 79% of theory.

EXAMPLE 185

6-[4-(3-Methyl-4-bromo-phenylsulfonyl)-butoxy]-carbostyril

Prepared analogous to Example 124 from 6-[4-(3-methyl-4-bromo-phenylmercapto)-butoxy]-carbostyril and hydrogen peroxide.
M.p.: 163°–167° C.
Yield: 57% of theory.

EXAMPLE 186

6-[4-(1,2,4-Triazol-3-yl-mercapto)-butoxy]-carbostyril

Prepared analogous to Example 122 from 6-(4-bromobutoxy)-carbostyril and 3-mercapto-1,2,4-triazole.
M.p.: 203°–206° C.
Yield: 82% of theory.

EXAMPLE 187

6-[4-(2,4,5-Trichlorophenyl-mercapto)-butoxy]-carbostyril

Prepared analogous to Example 122 from 6-(4-bromobutoxy)-carbostyril (m.p. 198°–199° C.) and 2,4,5-trichlorothiophenol.
M.p.: 177°–178° C.
Yield: 83% of theory.

EXAMPLE 188

6-[4-(2,4,5-Trichlorophenyl-sulfinyl)-butoxy]-carbostyril

Prepared analogous to Example 123 from 6-[4-(2,4-5-trichlorophenyl-mercapto)-butoxy]-carbostyril and hydrogen peroxide.
M.p.: 206°–208° C.
Yield: 98% of theory.

EXAMPLE 189

6-[4-(3,5-Dibromo-4-amino-phenylmercapto)-butoxy]-3,4-dihydrocarbostyril

Prepared analogous to Example 122 from 6-(4-bromobutoxy)-3,4-dihydro-carbostyril (m.p. 142°–147° C.) and 3,5-dibromo-4-amino-thiophenol.
M.p.: 90°–92° C.
Yield: 89% of theory.

EXAMPLE 190

6-[4-(3,5-Dibromo-4-amino-phenylsulfinyl)-butoxy]-3,4-dihydro-carbostyril

Prepared analogous to Example 123 from 6-[4-(3,5-dibromo-4-amino-phenylmercapto)-butoxy]-3,4-dihydro-carbostyril and hydrogen peroxide.
M.p.: 144°–146° C.
Yield: 76% of theory.

EXAMPLE 191

6-[4-(3,5-Dibromo-4-amino-phenylsulfonyl)-butoxy]-3,4-dihydro-carbostyril

Prepared analogous to Example 124 from 6-[4-(3,5-dibromo-4-amino-phenylsulfinyl)-butoxy]-3,4-dihydro-carbostyril and hydrogen peroxide.
M.p.: 157°–159° C.
Yield: 87% of theory.

EXAMPLE 192

6-[4-(3,5-Dibromo-4-amino-phenylmercapto)-butoxy]-carbostyril

Prepared analogous to Example 122 from 6-(4-bromobutoxy)-carbostyril (m.p. 198°–199° C.) and 3,5-dibromo-4-amino-thiophenol.
M.p.: 153°–155° C.
Yield: 86% of theory.

EXAMPLE 193

6-[4-(3,5-Dibromo-4-amino-phenylsulfinyl)-butoxy]-carbostyril

Prepared analogous to Example 123 from 6-[4-(3,5-dibromo-4-amino-phenylmercapto)-butoxy]-carbostyril and hydrogen peroxide.
M.p.: 205°–207° C.
Yield: 79% of theory.

EXAMPLE 194

6-[4-(3,5-Dibromo-4-amino-phenylsulfonyl)-butoxy]-carbostyril

Prepared analogous to Example 124 from 6-[4-(3,5-dibromo-4-amino-phenylmercapto)-butoxy]-carbostyril and hydrogen peroxide in formic acid.
M.p.: 238°–241° C.
Yield: 87% of theory.

EXAMPLE 195

6-[4-(4-Bromo-3-methyl-phenylmercapto)-butoxy]-3,4-dihydro-carbostyril

Prepared analogous to Example 122 from 6-(4-bromobutoxy)-3,4-dihydro-carbostyril (m.p. 142°–147° C.) and 4-bromo-3-methyl-thiophenol.
M.p: 104°–109° C.
Yield: 81% of theory.

EXAMPLE 196

6-[4-(4-Bromo-3-methyl-phenylsulfinyl)-butoxy]-3,4-dihydro-carbostyril

Prepared analogous to Example 123 from 6-[4-(4-bromo-3-methyl-phenylmercapto)-butoxy]-3,4-dihydro-carbostyril and hydrogen peroxide.
M.p.: 129°–130° C.
Yield: 75% of theory.

EXAMPLE 197

6-[4-(2,5-Dibromophenyl-mercapto)-butoxy]-3,4-dihydro-carbostyril

Prepared analogous to Example 122 from 6-(4-bromobutoxy)-3,4-dihydro-carbostyril (m.p.: 142°–147° C.) and 2,5-dibromo-thiophenol.
M.p.: 127°–129° C.
Yield: 75% of theory.

EXAMPLE 198

6-[4-(2,5-Dibromophenyl-sulfinyl)-butoxy]-3,4-dihydro-carbostyril

Prepared analogous to Example 123 from 6-[4-(2,5-dibromophenyl-mercapto)-butoxy]-3,4-dihydro-carbostyril and hydrogen peroxide.
M.p.: 182°–184° C.
Yield: 84% of theory.

EXAMPLE 199

6-[4-(2,5-Dibromophenyl-mercapto)-butoxy]-carbostyril

Prepared analogous to Example 122 from 6-(4-bromobutoxy)-carbostyril (m.p.: 198°–199° C.) and 2,5-dibromothiophenol.
M.p.: 178°–185° C.
Yield: 67% of theory.

EXAMPLE 200

6-[4-(2,5-Dibromophenyl-sulfinyl)-butoxy]-carbostyril

Prepared analogous to Example 123 from 6-[4-(2,5-dibromophenyl-mercapto)-butoxy]-carbostyril and hydrogen peroxide.
M.p.: 187°–189° C.
Yield: 45% of theory.

EXAMPLE 201

6-[3-(3,4-Dichlorophenyl-mercapto)-propoxy]-3,4-dihydro-carbostyril

Prepared analogous to Example 122 from 6-(3-bromopropoxy)-3,4-dihydro-carbostyril (m.p. 111°–118° C.) and 3,4-dichloro-thiophenol.
M.p.: 106°–107° C.
Yield: 76% of theory.

EXAMPLE 202

6-[3-(3,4-Dichlorophenyl-sulfinyl)-propoxy]-3,4-dihydro-carbostyril

Prepared analogous to Example 123 from 6-[3-(3,4-dichlorophenyl-mercapto)-propoxy]-3,4-dihydro-carbostyril and hydrogen peroxide.
M.p.: 170°–172° C.
Yield: 84% of theory.

EXAMPLE 203

6-[4-(4-Cyclohexylphenyl-mercapto)-butoxy]-3,4-dihydro-carbostyril

Prepared analogous to Example 122 from 6-(4-bromobutoxy)-3,4-dihydro-carbostyril (m.p.: 142°–147° C.) and 4-cyclohexyl-thiophenol.
M.p.: 118°–120° C.
Yield: 68% of theory.

EXAMPLE 204

6-[4-(4-Cyclohexylphenyl-sulfinyl)-butoxy]-3,4-dihydro-carbostyril

Prepared analogous to Example 123 from 6-[4-(4-cyclohexylphenyl-mercapto)-butoxy]-3,4-dihydro-carbostyril and hydrogen peroxide.
M.p.: 155°–157° C.
Yield: 65% of theory.

EXAMPLE 205

6-[4-(4-Cyclohexylphenyl-sulfonyl)-butoxy]-3,4-dihydro-carbostyril

Prepared analogous to Example 124 from 6-[4-(4-cyclohexylphenyl-mercapto)-butoxy]-3,4-dihydro-carbostyril and hydrogen peroxide.
M.p.: 172°–174° C.
Yield: 52% of theory.

EXAMPLE 206

6-[4-(4-Cyclohexylphenyl-mercapto)-butoxy]-carbostyril

Prepared analogous to Example 122 from 6-(4-bromobutoxy)-carbostyril (m.p. 188°–189° C.) and 4-cyclohexylthiophenol.
M.p.: 165°–167° C.
Yield: 64% of theory.

EXAMPLE 207

6-[4-(4-Cyclohexylphenyl-sulfinyl)-butoxy]-carbostyril

Prepared analogous to Example 123 from 6-[4-(4-cyclohexylphenyl-mercapto)-butoxy]-carbostyril and hydrogen peroxide.
M.p.: 188°–190° C.
Yield: 64% of theory.

EXAMPLE 208

6-[4-(4-Cyclohexylphenyl-sulfonyl)-butoxy]-carbostyril

Prepared analogous to Example 124 from 6-[4-(4-cyclohexylphenyl-mercapto)-butoxy]-carbostyril and hydrogen peroxide.
M.p.: 185°–186° C.
Yield: 87% of theory.

EXAMPLE 209

6-[4-(4-tert. Butylphenyl-mercapto)-butoxy]-3,4-dihydro-carbostyril

Prepared analogous to Example 122 from 6-(4-bromo-butoxy)-3,4-dihydro-carbostyril (m.p. 142°–147° C.) and 4-tert. butyl-thiophenol.
M.p.: 126°–127° C.
Yield: 86% of theory.

EXAMPLE 210

6-[4-(4-tert. Butylphenyl-sulfinyl)-butoxy]-3,4-dihydro-carbostyril

Prepared analogous to Example 123 from 6-[4-(4-tert. butylphenyl-mercapto)-butoxy]-3,4-dihydro-carbostyril and hydrogen peroxide.
M.p.: 121°–123° C.
Yield: 67% of theory.

EXAMPLE 211

6-[4-(4-tert. Butylphenyl-sulfonyl)-butoxy]-3,4-dihydro-carbostyril

Prepared analogous to Example 124 from 6-[4-(4-tert. butylphenyl-mercapto)-butoxy]-3,4-dihydro-carbostyril and hydrogen peroxide.
M.p. 198°–200° C.
Yield: 83% of theory.

EXAMPLE 212

6-[4-(4-tert. Butylphenyl-mercapto)-butoxy]-carbostyril

Prepared analogous to Example 122 from 6-(4-bromobutoxy)-carbostyril (m.p. 198°–199° C.) and 4-tert. butylthiophenol.
M.p.: 156°–158° C.
Yield: 63% of theory.

EXAMPLE 213

6-[4-(4-tert. Butylphenyl-sulfinyl)-butoxy]-carbostyril

Prepared analogous to Example 123 from 6-[4-(4-tert. butylphenyl-mercapto)-butoxy]-carbostyril and hydrogen peroxide.
M.p.: 164°–166° C.
Yield: 74% of theory.

EXAMPLE 214

6-[4-(4-tert. Butylphenyl-sulfonyl)-butoxy]-carbostyril

Prepared analogous to Example 124 from 6-[4-(4-tert. butylphenyl-mercapto)-butoxy]-carbostyril and hydrogen peroxide.
M.p.: 203°–205° C.
Yield: 56% of theory.

EXAMPLE 215

6-[4-(2-Quinolyl-sulfinyl)-butoxy]-3,4-dihydro-carbostyril

Prepared analogous to Example 123 from 6-[4-(2-quinolyly-mercapto)-butoxy]-3,4-dihydro-carbostyril and hydrogen peroxide.
M.p.: 154°–157° C.
Yield: 79% of theory.

EXAMPLE 216

6-[4-(2-Quinolyl-sulfonyl)-butoxy]-3,4-dihydro-carbostyril

Prepared analogous to Example 124 from 6-[4-(2-quinolyl-mercapto)-butoxy]-3,4-dihydro-carbostyril and hydrogen peroxide.
$R_f$-value: 0.50 (silica gel fluorescent plate; eluant: benzene/ethanol/conc. ammonia=75/25/2).
Yield: 72% of theory.

EXAMPLE 217

6-[2-(N-Methyl-N-cyclohexyl-carbamidomethyl-mercapto)-ethoxy]-3,4-dihydro-carbostyril Prepared analogous to Example 122 from 6-[2-chloro-ethoxy)-3,4-dihydro-carbostyril (m.p. 152.5°–153.5° C. and N-methyl-N-cyclohexyl-thioglycolic acid amide.
$R_f$-value: 0.46 (silica gel fluorescent plate; eluant: ethylenechloride/methanol=95/5).
Yield: 63% of theory.

EXAMPLE 218

6-[2-(N-Methyl-N-cyclohexyl-carbamidomethyl-sulfinyl)-ethoxy]-3,4-dihydro-carbostyril Prepared analogous to Example 123 from 6-[2-(N-methyl-N-cyclohexyl-carbamidomethyl-mercapto)-ethoxy]-3,4-dihydro-carbostyril and hydrogen peroxide.
$R_f$-value: 0.34 (silica gel fluorescent plate: eluant: ethylene chloride/methanol=95/5).
M.p.: 143°–146° C.
Yield: 48% of theory.

EXAMPLE 219

6-[2-(N-Methyl-N-cyclohexyl-carbamidomethyl-sulfonyl)-ethoxy]-3,4-dihydro-carbostyril Prepared analogous to Example 124 from 6-[2-(N-methyl-N-cyclohexyl-carbamidomethyl-mercapto)-ethoxy]-3,4-dihydro-carbostyril and hydrogen peroxide in formic acid.
$R_f$-value: 0.48 (silica gel fluorescent plate: eluant: ethylene chloride/methanol=95/5).
M.p.: 110°–111° C.
Yield: 45% of theory.

EXAMPLE 220

6-[2-(N-Methyl-N-cyclohexyl-carbamidomethyl-mercapto)-ethoxy]-carbostyril

Prepared analogous to Example 122 from 6-(2-chloroethoxy)-carbostyril [$R_f$-value: 0.30 (silica gel fluorescent plate; eluant: ethylene chloride/methanol=95/5)] and N-methyl-N-cyclohexyl-thioglycolic acid amide.
$R_f$-value: 0.41 (silica gel fluorescent plate: eluant: ethylene chloride/methanol=95/5).
Yield: 62% of theory.

EXAMPLE 221

6-[2-(N-Methyl-N-cyclohexyl-carbamidomethyl-sulfinyl)-ethoxy]-carbostyril

Prepared analogous to Example 123 from 6-[2-(N-methyl-N-cyclohexyl-carbamidomethyl-mercapto)-ethoxy]-carbostyril and hydrogen peroxide.
$R_f$-value: 0.027 (silica gel fluorescent plate: eluant: ethylene chloride/methanol=95/5).
M.p.: 128°–130° C.
Yield: 65% of theory.

EXAMPLE 222

6-[2-(N-Methyl-N-cyclohexyl-carbamidomethyl-sulfonyl)-ethoxy]-carbostyril

Prepared analogous to Example 124 from 6-[2-(N-methyl-N-cyclohexyl-carbamidomethyl-mercapto)-ethoxy]-carbostyril and hydrogen peroxide.
$R_f$-value: 0.39 (silica gel fluorescent plate; eluant: ethylene chloride/methanol=95/5).
Yield: 67% of theory.

EXAMPLE 223

6-[3-(3,4-Dichlorophenyl-sulfonyl)-propoxy]-3,4-dihydro-carbostyril

Prepared analogous to Example 124 from 6-[3-(3,4-dichlorophenyl-mercapto)-propoxy]-3,4-dihydro-carbostyril and hydrogen peroxide.
M.p.: 187°–188° C.

Yield: 87% of theory.

EXAMPLE 224

6-[5-(3,4-Dichlorophenyl-mercapto)-pentoxy]-3,4-dihydro-carbostyril

Prepared analogous to Example 122 from 6-(5-bromopentoxy)-3,4-dihydro-carbostyril (m.p.: 97°–98° C.) and 3,4-dichloro-thiophenol.
M.p.: 101°–104° C.
Yield: 69% of theory

EXAMPLE 225

6-[5-(3,4-Dichlorophenyl-sulfinyl)-pentoxy]-3,4-dihydro-carbostyril

Prepared analogous to Example 123 from 6-[5-(3,4-dichlorophenyl-mercapto)-pentoxy]-3,4-dihydro-carbostyril and hydrogen peroxide.
M.p.: 165°–166° C.
Yield: 74% of theory.

EXAMPLE 226

6-[5-(3,4-Dichlorophenyl-sulfonyl)-pentoxy]-3,4-dihydro-carbostyril

Prepared analogous to Example 124 from 6-[5-(3,4-dichlorophenyl-mercapto)-pentoxy]-3,4-dihydro-carbostyril and hydrogen peroxide.
M.p.: 176°–178° C.
Yield: 65% of theory.

EXAMPLE 227

6-[4-(2-Methyl-4-tert. butylphenyl-mercapto)-butoxy]-3,4-dihydro-carbostyril

Prepared analogous to Example 122 from 6-(4-bromobutoxy)-3,4-dihydro-carbostyril (m.p.: 142°–147° C.) and 2-methyl-4-tert. butyl-thiophenol.
M.p.: 81°–85° C.
Yield: 91% of theory.

EXAMPLE 228

6-[4-(2-Methyl-4-tert. butylphenyl-sulfinyl)-butoxy]-3,4-dihydro-carbostyril

Prepared analogous to Example 123 from 6-[4-(2-methyl-4-tert. butylphenyl-mercapto)-butoxy]-3,4-dihydro-carbostyril and hydrogen peroxide. Resinous substance. $R_f$-value: 0.54 (silica gel fluorescent plate; eluant: ethylene chloride/methanol=95/5).

EXAMPLE 229

6-[4-(3,5-Dichloro-4-hydroxyphenyl-mercapto)-butoxy]-3,4-dihydro-carbostyril

Prepared analogous to Example 122 from 6-(4-bromo-butoxy)-3,4-dihydro-carbostyril (m.p.: 142°–147° C.) and 3,4-dichloro-4-hydroxy-thiophenol in an atmosphere of nitrogen as protective gas.
M.p.: 110°–114°
Yield: 94% of theory.

EXAMPLE 230

5-Bromo-6-(4-phenylmercapto-butoxy)-carbostyril

Prepared analogous to Example 122 from 5-bromo-6-(4-bromo-butoxy)-carbostyril [prepared by bromination of 6-(4-bromo-butoxy)-carbostyril] and thiophenol.
M.p.: 209°–213° C.
Yield: 41% of theory.

EXAMPLE 231

5-Nitro-6-(4-phenylmercapto-butoxy)-carbostyril

Prepared analogous to Example 122 from 5-nitro-6-(4-bromo-butoxy)-carbostyril [m.p. 250° C., prepared by nitration of 6-(4-bromo-butoxy)-3,4-dihydro-carbostyril] and thiophenol.
M.p.: 228°–230° C.
Yield: 71% of theory.

EXAMPLE 232

5-Nitro-6-(4-phenylsulfinyl-butoxy)-carbostyril

Prepared analogous to Example 123 from 5-nitro-6-(4-phenyl-mercapto-butoxy)-carbostyril and hydrogen peroxide.
M.p. 192°–194° C.
Yield: 91% of theory.

EXAMPLE 233

5-Acetamino-6-(4-phenylmercapto-butoxy)-carbostyril

Prepared analogous to Example 122 from 5-acetamino-6-(4-bromo-butoxy)-carbostyril [prepared by reduction with zinc in acetic acid of 5-nitro-6-(4-bromo-butoxy)-carbostyril in the presence of acetic acid anhydride] and thiophenol.
M.p. 238°–240° C.
Yield: 80% of theory.

EXAMPLE 234

5-Acetamino-6-(4-phenylsulfinyl-butoxy)-carbostyril

Prepared analogous to Example 123 from 5-acetamino-6-(4-phenylmercapto-butoxy)-carbostyril and hydrogen peroxide.
M.p.: 213°–217° C.
Yield: 47% of theory.

EXAMPLE 235

5-Bromo-6-(4-phenylsulfinyl-butoxy)-carbostyril

Prepared analogous to Example 123 from 5-bromo-6-(4-phenyl-mercapto-butoxy)-carbostyril and hydrogen peroxide.
M.p.: 190°–191° C.
Yield: 82% of theory.

EXAMPLE 236

4-Methyl-6-[4-(2-pyridyl-sulfinyl)-butoxy]-carbostyril

A solution of 0.170 gm (0.0005 mol) of 4-methyl-6-[4-(2-pyridyl-mercapto)-butoxy]-carbostyril in 5 ml of glacial acetic acid and a solution of 0.107 gm (0.0005 mol) of sodium metaperiodate in 6 ml of water were admixed and allowed to stand at room temperature for 22 hours. Subsequently, the light brown reaction solution was diluted with 20 ml of water, and the reaction product was extracted with chloroform. The extract was shaken once with an aqeuous sodium carbonate solution and dried over anhydrous magnesium sulfate. After evaporating the organic phase, the residue was recrystallized from toluene.
M.p.: 166°–168° C.
Yield: 0.04 gm (22.5% of theory).

EXAMPLE 237

6-(4-tert. Butylsulfinyl-butoxy)-3,4-dihydro-carbostyril

Prepared analogous to Example 123 from 6-(4-tert. butyl-mercapto-butoxy)-3,4-dihydro-carbostyril (m.p. 117°–118° C.) and hydrogen peroxide.
M.p.: 126°–128° C.
Yield: 62% of theory.

EXAMPLE 238

6-[4-(3-Hydroxy-pyrid-2-yl-mercapto)-butoxy]-3,4-dihydro-carbostyril

Prepared analogous to Example 122 from 6-(4-bromo-butoxy)-3,4-dihydro-carbostyril (m.p. 142°–147° C.) and 3-hydroxy-2-mercapto-pyridine.
M.p.: 211°–216° C.
Yield: 58% of theory.

EXAMPLE 239

6-[4-(1,2,4-Triazol-3-yl-sulfinyl)-butoxy]-carbostyril

Prepared analogous to Example 123 from 6-[4-(1,2,4-triazol-3-yl-mercapto)-butoxy]-carbostyril and hydrogen peroxide.
$R_f$-value: 0.12 (silica gel fluorescent plate; eluant ethylene chloride/methanol=95/5).

EXAMPLE 240

6-[4-(1,2,4-Triazol-3-yl-mercapto)-butoxy]-3,4-dihydro-carbostyril

Prepared analogous to Example 122 from 6-(4-bromo-butoxy)-3,4-dihydro-carbostyril (m.p. 142°–147° C.) and 3-mercapto-1,2,4-triazole.
M.p.: 152°–154° C.
Yield: 82% of theory.

EXAMPLE 241

6-[4-(1,2,4-Triazol-3-yl-sulfinyl)-butoxy]-3,4-dihydro-carbostyril

Prepared analogous to Example 123 from 6-[4-(1,2,4-triazol-3-yl-mercapto)-butoxy]-3,4-dihydro-carbostyril and hydrogen peroxide.
$R_f$-value: 0.18 (silica gel fluorescent plate; eluant: ethylene chloride/methanol=95/5).

EXAMPLE 242

6-[4-(1,2,4-Triazol-3-yl-sulfonyl)-butoxy]-3,4-dihydro-carbostyril

Prepared analogous to Example 124 from 6-[4-(1,2,4-triazol-3-yl-mercapto)-butoxy]-3,4-dihydro-carbostyril and hydrogen peroxide.
$R_f$-value: 0.22 (silica gel fluorescent plate; eluant: ethylene chloride/methanol=95/5).
M.p.: 217°–224° C.

EXAMPLE 243

6-[4-(2,4,5-Trichlorophenyl-mercapto)-butoxy]-3,4-dihydro-carbostyril

Prepared analogous to Example 122 from 6-(4-bromo-butoxy)-3,4-dihydro-carbostyril (m.p.: 142°–147° C.) and 2,4,5-trichloro-thiophenol.
M.p.: 144°–145° C.
Yield: 87% of theory.

The compounds of this invention, that is, those embraced by Formula I above, have useful pharmacodynamic properties. More particularly, the exhibit cardiotonic, especially positive inotropic, and antithrombotic activities in warm-blooded animals, such as mice and rats.

The above pharmacological properties were ascertained by means of the standard test methods described below, and the tables show the results of these tests for a few representative species of the genus, where A = 6-(4-Phenylmercapto-butoxy)-3,4-dihydro-carbostyril,
B = 6-(4-Phenylsulfinyl-butoxy)-3,4-dihydro-carbostyril,
C = 6-(4-Phenylsulfonyl-butoxy)-3,4-dihydro-carbostyril,
D = 6-[4-(2-Pyridyl-mercapto)-butoxy]-3,4-dihydro-carbostyril,
E = 6-[4-(2-Pyridyl-sulfinyl)-butoxy]-3,4-dihydro-carbostyril,
F = 6-[4-(2-Pyridyl-sulfonyl)-butoxy]-3,4-dihydro-carbostyril,
G = 6-(2-Phenylsulfinyl-ethoxy)-3,4-dihydro-carbostyril,
H = 6-(4-Benzylsulfinyl-butoxy)-3,4-dihydro-carbostyril,
I = 6-[4-(4-Chlorophenyl-sulfinyl)-butoxy]-3,4-dihydro-carbostyril,
K = 6-(4-Cyclohexylsulfinyl-butoxy)-3,4-dihydro-carbostyril,
L = 6-[4-(2-Naphthyl-sulfinyl)-butoxy]-3,4-dihydro-carbostyril,
M = 6-[4-(2-Methoxyphenyl-sulfinyl)-butoxy]-3,4-dihydro-carbostyril,
N = 6-(4-Phenylsulfinyl-butoxy)-carbostyril,
O = 6-[4-(4-Hydroxy-3,5-di-tert. butylphenyl-sulfinyl)-butoxy]-carbostyril,
P = 6-[4-(3,4-Dichlorophenyl-sulfinyl)-butoxy]-carbostyril,
Q = 4-Methyl-6-(4-phenylsulfinyl-butoxy)-carbostyril,
R = 6-[4-(3,4-Dichlorophenyl-sulfonyl)-butoxy]-3,4-dihydro-carbostyril,
S = 6-[4-(2,5-Dichlorophenyl-sulfinyl)-butoxy]-3,4-dihydro-carbostyril,
T = 6-[4-(2-Pyridyl-sulfonyl)-butoxy]-carbostyril,
U = 6-[4-(3,4-Dichlorophenyl-sulfinyl)-butoxy]-3,4-dihydro-carbostyril,
V = 6-[4-(4-Biphenylylsulfinyl)-butoxy]-carbostyril,
W = 6-[4-(2-Quinolylsulfinyl)-butoxy]-carbostyril,
X = 6-(4-Cyclohexylsulfinyl-butoxy)-carbostyril,
Y = 5-Bromo-6-(4-phenylsulfinyl-butoxy)-carbostyril,
Z = 6-[2-(N-Methyl-N-cyclohexyl-carbamidomethyl-sulfinyl)-ethoxy]-carbostyril,
AA = 6-[4-(3,5-Dibromo-4-aminophenylsulfinyl)-butoxy]-3,4-dihydrocarbostyril,
BB = 6-[4-(3,5-Dibromo-4-aminophenylsulfinyl)-butoxy]-carbostyril,
CC = 6-[4-(4-Cyclohexylphenylsulfinyl)-butoxy]-3,4-dihydro-carbostyril,
DD = 6-[4-(4-Cyclohexylphenylsulfinyl)-butoxy]-carbostyril,
EE = 6-[4-(4-tert.-Butylphenylsulfinyl)-butoxy]-carbostyril,
FF = 6-[4-(3,4-Dichlorophenylsulfinyl)-butoxy]-3,4-dihydrocarbostyril,
GG = 6-[5-(2-Pyridylsulfinyl)-pentoxy]-3,4-dihydrocarbostyril,
HH = 6-(4-tert.Butylsulfinyl-butoxy)-3,4-dihydrocarbostyril,
II = 8-(4-Phenylmercapto-butoxy)-3,4-dihydro-carbostyril, JJ=6-[4-(2-Pyridylsulfinyl)-butoxy]-carbostyril,
KK=4-Methyl-6-[4-(2-pyridylsulfinyl)-butoxy]-carbostyril, and
LL=6-[4-(4-Cyclohexyl-phenylsulfinyl)-butoxy]-carbostyril.

1. Determination of the thrombocyte aggregation inhibiting activity by the method of Born and Cross [J. Physiol. 170, 397 (1964)]:

The thrombocyte aggregation was measured in the platelet-rich plasma of healthy human donors. The decrease in optical density was measured and recorded photometrically after the addition of adenosine diphosphate or collagen. From the angle of inclination of the density curve, the rate of aggregation was estimated (Vmax). The optical density was taken as the point on the curve where the most light was transmitted (O.D.).

The $EC_{50}$ values in the tables indicate the optical density.

Small doses of collagen were chosen, but sufficient to give irreversible aggregation. To provoke maximum aggregation, about 0.01 ml of the collagen solution was added to 1 ml of platelet-rich plasma. (Commercial collagen of Hormonchemie, Munich). The adenosine diphosphate (ADP) doses were chosen to give only the first phase of the BORN curve. The necessary amount of ADP was about $1 \times 10^{-6}$ mol/l. Commercial ADP of Boehringer Mannheim was used.

The substance dose which produced a 50% inhibition of the thrombozytes aggregation ($EC_{50}$) was determined graphically.

TABLE I

| Compound | $EC_{50}$ $10^{-6}$ mol/liter | |
|---|---|---|
| | Collagen | ADP |
| A | 50 | >100 |
| B | 4 | 20 |
| C | 5 | 15 |
| D | 45 | >100 |
| E | 6.5 | 25 |
| F | 20 | 20 |
| G | 3.5 | 17 |
| H | 2.5 | 14 |
| I | 4 | 10 |
| K | 4.5 | 12 |
| L | 1 | 10 |
| M | 4 | 22 |
| N | 0.6 | 3 |
| O | 0.2 | 0.5 |
| P | 0.2 | 1.8 |
| Q | 3.6 | 40 |
| R | 1.5 | 25 |
| S | 1.0 | 10 |
| T | 0.1 | 6 |
| U | 4 | 15 |

2. Determination of the prolongation of the bleeding time: Preface:

The human organism and the warm-blooded animal have an ingenious mechanism which protects them from blood loss in case of injuries. This system consists of blood platelets (thrombocytes), which quickly occlude the side of vessel injury by means of their adhesiveness (primary hemostasis). Besides this cellular hemostasis mechanism, the body has the blood coagulation system. In this system plasma factors (proteins) are activated into an effective form, which finally convert liquid plasma fibringen into fibrin coagulum. The system of primary hemostasis, which mainly consists of thrombocytes, and the coagulation system complement each other, both having the common purpose to protect the body effectively against blood loss.

In some diseases it happens, that also in an intact blood vessel coagulation occurs and thrombocytes aggregate. The effect on the coagulation system of cumarin or of heparin is known and can easily be measured by coagulation tests which show a prolongation under the influence of these substances. (Plasma-recalcif. time, Quick-Test, Thrombin time, etc.).

The function of the thrombocytes can be determined by measuring the bleeding time. The normal bleeding time in human beings is in the range of 1 to 3 minutes and needs intact thrombozytes in a sufficient number. If the number of thrombocytes is normal and the bleeding time is prolonged, this signifies a disturbed function of the thrombocytes. This is found in some congenital defects of thrombocyte function (V. Willebrand's disease, for example). If, on the other hand it is the aim to prevent spontaneous aggregation of the thrombocytes and occlusion in the arterial system by antithrombotic drugs, the bleeding time should be prolonged as a consequence. Therefore, using antithrombotic substances, a prolongation of the bleeding time is expected. If the plasma coagulation system is not influenced by such a medicine, coagulation tests will give a normal result.

Literature: W. D. Keidel: *Kurzgefasstes Lehrbuck der Physiologie,* Georg Thieme Verlag, Stuttgart, Germany, 1967, page 31: The Mechanism of Hemostasis.

To measure the bleeding time, 10 mg/kg of the test compound is administered orally to conscious mice. After 1 hour, 0.5 mm of the tip of the mousetail is cut off and droplets of blood are gently removed with filter paper every 30 second. The number of drops of blood give a measure for the bleeding time (5 animals/experiment).

The numbers in the following table represent the prolongation in % compared to the control group.

TABLE II

| Compound | Prolongation of the bleeding time in % after one hour |
|---|---|
| A | 145 |
| B | 102 |
| C | 26 |
| D | 76 |
| E | 152 |
| F | 91 |
| G | 5 |
| H | 29 |
| I | >300 |
| K | 12 |
| L | 15 |
| M | 27 |
| O | 73 |
| P | 12 |
| Q | 39 |
| R | 30 |
| T | 5 |
| U | 33 |

3. Determination of the positive inotropic activity:

Rats were anesthetized with ether and subsequently killed by a blow on the neck. After opening the thorax, the heart was removed and both auricles were separated. The auricles were put into an organ bath of 100 ml containing a tyrode solution at a temperature of 30° C. The tyrode solution was infused with carbogen (95% of $O_2$ and 5% of $CO_2$). The spontaneous contractions of the auricles were registered isometrically. The auricles were weighted with 1 gm. The compounds in question were tested on 4 auricles each at $1 \times 10^{-5}$ gm/ml. The alteration of the contraction force was registered in % from the starting values. The following table gives the obtained results:

TABLE III

| Substance | % Increase in Force of Contraction |
|---|---|
| B | 30 |
| C | 35 |
| E | 16 |
| F | 18 |
| I | 52 |
| L | 63 |
| M | 65 |
| Q | 58 |
| S | 83 |
| T | 32 |

4. PDE Inhibition

Principle:

cAMP is hydrolysed to AMP by phosphodiesterase (PDE) from various sources, including blood platelets. This hydrolysis is inhibited by PDE inhibitors according to the concentration.

Method:

The phosphodiesterase used was the 10,000×g supernatant of human blood platelets which had been frozen with water and thawed out again.

An amount of 0.3 ml of a mixture which contained 0.1 mole/liter of trihydroxy-aminomethane (pH 7.4), 3 mmole/liter of magnesium chloride, 1 mmole/liter of AMP, 1 μmol/liter of $^3$H-cAMP (specific activity about 10 MBq/μmol), PDE as well as the substance to be tested and water for the control were incubated for 15 minutes at 37° C.

The incubation was stopped by the addition of 0.5 ml of zinc sulfate (0.266 mole/liter) and 0.5 ml of barium hydroxide (0.266 mole/liter), the precipitate was centrifuged and the activity remaining in the supernatant of the unreacted $^3$H-cAMP was determined. From a comparison of the substance preparations and the control preparations, the concentration for a 50% inhibiting activity (IC$_{50}$) of the respective substance was calculated. The results are set forth in the following table:

TABLE IV

| Substance | IC$_{50}$ (μMol/l) |
|---|---|
| A | 0.78 |
| B | 1.9 |
| C | 1.5 |
| D | 1.6 |
| E | 3.9 |
| F | 3.8 |
| G | 3.4 |
| H | 1.6 |
| I | 0.8 |
| K | 2.5 |
| L | 0.14 |
| M | 0.15 |
| N | 0.47 |
| O | 0.079 |
| P | 0.22 |
| Q | 0.64 |
| R | 1.8 |
| S | 2.1 |
| T | 1.0 |
| U | 0.27 |
| V | 0.12 |
| W | 0.14 |
| X | 0.7 |
| Y | 0.1 |
| Z | 0.5 |
| AA | 0.25 |
| BB | 0.05 |
| CC | 1.6 |
| DD | 0.04 |

TABLE IV-continued

| Substance | IC$_{50}$ (μMol/l) |
|---|---|
| EE | 0.03 |
| FF | 0.27 |

According to GASTPAR (see Thrombosis Research, 5, 277–289, 1974) substances, which inhibit platelet phosphodiesterase and thereby are inhibitors of platelet aggregation, assist also in the inhibition of lodgment of tumor cells. Here, the substances to be tested are applied before the tumor cell injection and the survival rate of the test animals, for example rats, is determined against controls.

5. Influence on Platelet Thromboses in the Rat

Method:

Literature: H. Poliwoda, J. Lilli, G. Hagemann, D. Schyma: Z. ges. exp. Med., 145, 252 (1968)

Male rats (body weight between 70 and 90 grams) received an intraperitoneal Nembutal anesthesia (dose: 50 to 60 mg/kg). To avoid hypothermia, they were positioned on a heated test table (about 37° C.). The respiratory passage was held free by insertion of a tracheal cannula.

After a transverse abdominal incision was made, an intestinal loop was exposed and fixed, and a vein, with a diameter of about 300 μ was prepared. A monopolar platinum electrode embedded in glass and having a tip diameter of about 100μ was applied to the vein as an irritating cathode. The indifferent electrode was applied to the same vessel opposite the cathode. The irritation was provoked by 150 volts of direct current for a period of 100 milliseconds. After the irritation, the area of observation was continuously rinsed with warm (37° C.) physiological salt solution.

The formation and growth of the thrombosis was followed under a binocular microscope over a time period of 20 minutes. During the entire period of observation, the percentage of the vessel volume closed by the thrombosis was estimated at different time intervals.

Five animals per dose were used, and the results were averaged.

In the test compound experiments, the average size of the thrombosis in the treated animal group was compared with that of an untreated animal group. The result was given as "percentage reduction of the average thrombosis size." The following table contains the values obtained.

TABLE V

| Substance* | Percentage Reduction of the Average Thrombosis Size |
|---|---|
| B | 23 |
| E | 16 |
| I | 4 |
| N | 24 |
| O | 17 |
| P | 15 |
| Q | 22 |
| T | 29 |
| U | 32 |
| HH | 19 |
| II | 4 |
| JJ | 29 |
| KK | 17 |
| LL | 11 |

*The remaining substances were not tested.

6. Effect on Tumor Cell Embolism (a) Mice having a body weight of about 25 grams received an injection in the jugular vein of a million Walker-256 carcinosarcoma cells. These tumor cells lead to a formation of thrombocyte clumps, which causes a fatal tumor cell embolism in a portion of the animals. Under the influence of the test compounds, the number of deceased animals can be reduced. Normally, about 65% of the control animals died within 10 minutes as a result of pulmonary embolism.

The results of the testing are set forth in the following table:

TABLE VI

| Substance | Percentage of Deceased Animals Dose (mg/kg p.o.)* | | Control Group** |
|---|---|---|---|
| | 2 | 6 | |
| T+ | 23% | 6.7% | 62.5% |
| U+ | 40% | 13% | 65.6% |

*For a group of 30 animals.
**For a group of 40 animals.
+At a dose of 8 mg/kg p.o., 0% of animals died.

(b) By virtue of the injection of tumor cells, a strong decrease in the number of thrombocytes in the blood was produced in the test animals (rats) as a consequence of thrombocyte and tumor cell thrombocyte aggregation. Thirty minutes after the intravenous tumor cell injection, the surviving animals exhibited a reduction of about 70% over the average starting value before the test. By administration of suitable substances, the extent of the thrombocyte decrease can be reduced as compared to that of the untreated control animals.

The results are set forth in the following table:

TABLE VII

Percent Reduction in the Number of Thrombocytes After Intravenous Administration of Tumor Cells

| Substance | Dose (mg/kg) | n Control 14 | % Reduction of the Number of Thrombocytes 70 |
|---|---|---|---|
| T | 2 | 22 | 29 |
| | 4 | 28 | 15 |
| | 8 | 30 | 1.1 |
| U | 2 | 18 | 34 |
| | 6 | 26 | 20.8 |
| | 18 | 30 | 1.1 |

7. Acute Toxicity:

The acute toxicity of the test compounds was determined on groups of 10 mice each after oral administration of a single dose of 1,000 mg/kg (observation time: 14 days).

TABLE VIII

| Substance | Acute Toxicity per os | |
|---|---|---|
| A | >1,000 mg/kg | (0 out of 10 animals died) |
| B | >1,000 mg/kg | (0 out of 10 animals died) |
| C | >1,000 mg/kg | (0 out of 10 animals died) |
| D | >1,000 mg/kg | (0 out of 10 animals died) |
| E | >1,000 mg/kg | (0 out of 10 animals died) |
| F | >1,000 mg/kg | (0 out of 10 animals died) |
| G | >1,000 mg/kg | (0 out of 10 animals died) |
| H | >1,000 mg/kg | (0 out of 10 animals died) |
| I | >1,000 mg/kg | (0 out of 10 animals died) |
| K | >1,000 mg/kg | (0 out of 10 animals died) |
| L | >1,000 mg/kg | (0 out of 10 animals died) |
| M | >1,000 mg/kg | (0 out of 10 animals died) |
| O | >1,000 mg/kg | (0 out of 10 animals died) |
| P | >1,000 mg/kg | (0 out of 10 animals died) |
| Q | >1,000 mg/kg | (0 out of 10 animals died) |
| R | >1,000 mg/kg | (0 out of 10 animals died) |

TABLE VIII-continued

| Substance | Acute Toxicity per os | |
|---|---|---|
| S | >1,000 mg/kg | (0 out of 10 animals died) |
| T | >1,000 mg/kg | (0 out of 10 animals died) |
| U | >1,000 mg/kg | (0 out of 10 animals died) |
| FF | >1,000 mg/kg | (0 out of 10 animals died) |

Based on their pharmacological properties, the novel compounds of the formula I are useful for the prophylaxis of thrombo-embolic diseases such as coronary infarct, cerebral infarct, so-called transient ischemic attacks, amaurosis fugax as well as the prophylaxis of arteriosclerosis and tumor metastasis.

For pharmaceutical purposes the compounds of the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.8 to 3.0 mg, preferably from 2.0 to 3.0 mg, and most preferably about 2.5 mg, per kg of body weight. A single dose in humans would be about 100 to 300 mg. The daily dose rate is from 1.6 to 9.0 mg, preferably from 4.0 to 9.0 mg, most preferably from 5.0 to 7.5 mg, per kg of body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 244

Tablets

The tablet composition is compounded from the following ingredients:

| | | |
|---|---|---|
| 6-[4-(2-Pyridyl-sulfinyl)-butoxy]-3,4-dihydro-carbostyril | 100.0 | parts |
| Lactose | 80.0 | parts |
| Corn Starch | 34.0 | parts |
| Polyvinylpurrolidone | 4.0 | parts |
| Magnesium stearate | 2.0 | parts |
| Total: | 220.0 | parts |

Preparation:

The active ingredient, the lactose and the corn starch are intimately admixed with each other, the mixture is uniformly moistened with an aqueous solution of the polyvinylpyrrolidone, the moist mass is granulated by passing it through a 2.0 mm-mesh screen, and the granulate is dried at 50° C. and passed through a 1.5 mm-mesh screen. The dry granulate is admixed with the magnesium stearate, and the composition is compressed into 220 mgm-tablets. Each tablet is an oral dosage unit composition containing 100 mgm of the active ingredient.

EXAMPLE 245

Coated Pills

The pill core composition is compounded from the following ingredients:

| | |
|---|---|
| 6-(4-Phenylsulfinyl-butoxy)-3,4-dihydro-carbostyril | 50.0 parts |
| Lactose | 40.0 parts |
| Corn Starch | 17.0 parts |
| Polyvinylpyrrolidone | 2.0 parts |
| Magnesium stearate | 1.0 parts |
| Total | 110.0 parts |

Preparation:

The ingredients were admixed and granulated as described in the preceding example, and after adding the magnesium stearate to the dry granulate, the composition was compressed into 110 mgm-pill cores which are subsequently coated with a thin shell of polyvinylpyrrolidone and a conventional sugar coating. Each coated pill is an oral dosage unit composition containing 50 mgm of the active ingredient.

EXAMPLE 246

Gelatin Capsules

The capsule filler composition is compounded from the following ingredients:

| | |
|---|---|
| 6-[4-(2-Pyridyl-sulfinyl)-butoxy]-3,4-dihydro-carbostyril | 100.0 parts |
| Corn starch, dry | 130.0 parts |
| Lactose, pulverized | 87.0 parts |
| Magnesium stearate | 3.0 parts |
| Total | 320.0 parts |

Preparation:

The ingredients are admixed with each other, the mixture is passed through a 0.75 mm-mesh screen and then homogenized, and 320 mgm-portions of the resulting composition are filled into No. 1 hard gelatin capsules. Each capsule is an oral dosage unit containing 100 mgm of the active ingredient.

EXAMPLE 247

Suppositories

The suppository composition is compounded from the following ingredients:

| | |
|---|---|
| 6-(4-Phenylsulfinyl-butoxy)-3,4-dihydro-carbostyril | 150.0 parts |
| Polyethyleneglycol 1500 | 550.0 parts |
| Polyethyleneglycol 6000 | 460.0 parts |
| Polyoxyethylene sorbitan monostearate | 840.0 parts |
| Total | 2,000.0 parts |

Preparation:

The polyethyleneglycols and the polyoxyethylene sorbitan monsstearate are admixed with each other, the mixture is melted, and the active ingredient is homogeneously blended into the molten mass. 2000 mgm-portions of the resulting composition are filled into cooled suppository molds and allowed to harden therein. Each suppository is a rectal dosage unit composition containing 150 mgm of the active ingredient.

EXAMPLE 248

Suspension

The suspension is compounded from the following ingredients:

| | |
|---|---|
| 6-[4-(2-Pyridyl-sulfinyl)-butoxy]-3,4-dihydro-carbostyril | 1.0 parts |
| Sodium salt of carboxymethyl cellulose | 0.1 parts |
| Methyl p-hydroxy-benzoate | 0.05 parts |
| Propyl p-hydroxy-benzoate | 0.01 parts |
| Cane Sugar | 10.0 parts |
| Glycerin | 5.0 parts |
| Sorbitol solution, 70% | 20.0 parts |
| Flavoring | 0.3 parts |
| Distilled water q.s. ad | 100.0 parts by vol. |

Preparation:

The distilled water is heated to 70° C., and the p-hydroxy-benzoates, the glycerin and the carboxymethyl cellulose salt are dissolved therein while stirring. The solution is cooled to room temperature, and the active ingredient is homogeneously suspended therein by stirring.

The sugar, the sorbitol solution and the flavoring are then added and dissolved in the suspension, and it is deaerated by stirring in vacuo. 5 ml of the suspension are an oral dosage unit composition containing 50 mgm of the active ingredient.

EXAMPLE 249

Tablets

Composition of one tablet:

| | |
|---|---|
| 6-[4-(2-pyridylsulfonyl)-butoxy]-3,4-dihydrocarbostyril | 100.0 mg |
| Lactose | 80.0 mg |
| Corn starch | 34.0 mg |
| Polyvinylpyrrolidone | 4.0 mg |
| Magnesium stearate | 2.0 mg |
| Total: | 220.0 mg |

Preparation:

The tablets are prepared using the procedure described in Example 244. The tablets have a diameter of 10 mm and are biplanar with facet on both sides and a dividing notch on one side.

EXAMPLE 250

Hard Gelatin Capsules

Composition of one capsule:

| | | |
|---|---|---|
| 6-[4-(3,4-Dichlorophenylsulfinyl-butoxy]-3,4-dihydrocarbostyril | | 150.0 mg |
| Corn starch, dry | about | 180.0 mg |
| Lastose, powdered | about | 87.0 mg |
| Magnesium stearate | | 3.0 mg |
| | Total: | 320.0 mg |

Preparation:

The capsules are prepared using the procedure described in Example 246. Each capsule is an oral dosage unit containing 150.0 mg of the active ingredient.

EXAMPLE 251

Suppositories

Composition of one suppository:

| | |
|---|---|
| 6-(4-Phenylsulfonyl-butoxy)-3,4-dihydro-carbostyril | 150.0 mg |
| Polyethylene glycol 1500 | 550.0 mg |

| | |
|---|---|
| Polyethylene glycol 6000 | 460.0 mg |
| Polyoxythylene sorbitan monostearate | 840.0 mg |
| Total: | 2,000.0 mg |

Preparation:
After the suppository mass has been melted, the active substance is distributed homogeneously therein and the melt is poured into pre-cooled molds.

EXAMPLE 252

Suspension

Composition of 100 ml of suspension:

| | | |
|---|---|---|
| 6-[4-(2-pyridylsulfonyl)-butoxy]-3,4-dihydrocarbostyril | 1.0 | g |
| Carboxymethylcellulose sodium salt | 0.1 | g |
| Methyl p-hydroxy benzoate | 0.05 | g |
| Propyl p-hydroxy-benzoate | 0.01 | g |
| Cane sugar | 10.0 | g |
| Glycerin | 5.0 | g |
| Sorbitol solution, 70% | 20.0 | g |
| Aroma | 0.3 | g |
| Distilled water q.s. ad | 100 | ml |

Preparation:
The suspension is prepared using the procedure described in Example 248. 5 ml of the suspension are an oral dosage unit composition containing 50 mg of the active ingredient.

EXAMPLE 253

Tablets

Composition of one tablet:

| | |
|---|---|
| 6-[2-(3,4-Dichlorophenylsulfinyl)-butoxy]-3,4-dihydro-carbostyril | 150.0 mg |
| Lactose, powdered | 89.0 mg |
| Corn starch | 40.0 mg |
| Colloidal silicic acid | 10.0 mg |
| Polyvinylpyrrolidone | 10.0 mg |
| Magnesium stearate | 1.0 mg |
| Total: | 300.0 mg |

Preparation:
The active substance mixed with lactose, corn starch, and silicic acid is moistened with a 20% aqueous polyvinyl pyrrolidone solution and passed through a screen of 1.5 mm mesh size. The granulate dried at 45° C. is again passed through the same screen and mixed with the specified quantity of magnesium stearate. Tablets are pressed from the mixture.

| | |
|---|---|
| Tablet weight: | 300 mg |
| Die: | 10 mm, flat |

EXAMPLE 254

Coated Tablets

Composition of one tablet core:

| | |
|---|---|
| 6-[4-(2-Pyridylsulfonyl)-butoxy]-3,4-dihydrocarbostyril | 75.0 mg |
| Calcium phosphate | 93.0 mg |
| Corn starch | 35.5 mg |
| Polyvinylpyrrolidone | 10.0 mg |
| Hydroxypropylmethylcellulose | 15.0 mg |
| Magnesium stearate | 1.5 mg |
| Total: | 230.0 mg |

Preparation:
The active substance is mixed with calcium phosphate, corn starch, polyvinyl-pyrrolidone, hydroxypropylmethyl-cellulose, and half the specified quantity of magnesium stearate. On a tabletting machine pressed articles are made with a diameter of about 13 mm which are passed on a suitable machine through a screen of 1.5 mm mesh size and mixed with the remaining quantity of magnesium stearate. This granulate is pressed on a tabletting machine into tablets of the desired form.

| | |
|---|---|
| Core weight: | 230 mg |
| Die: | 9 mm, curved. |

The coated tablet cores prepared in this way are covered with a coating consisting essentially of hydroxypropylmethylcellulose. The finished coated tablets are polished with beeswax.

| | |
|---|---|
| Coated pill weight: | 245 mg |

Any one of the other compounds embraced by formula I may be substituted for the particular active ingredient in Examples 244 through 254. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:
1. A compound of the formula

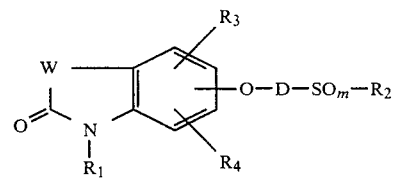

wherein
W is vinylene, methyl-vinylene, or ethylene;
m is 0, 1, or 2;
D is straight or branched alkylene of 2 to 6 carbon atoms, straight or branched hydroxy-alkylene of 3 to 6 carbon atoms, or xylylene;
$R_1$ is hydrogen or alkyl of 1 to 3 carbon atoms;
$R_2$ is cycloalkyl of 3 to 6 carbon atoms; aryl of 6 or 10 carbon atoms, alkylaryl of 7 to 10 carbon atoms, or aralkyl of 7 to 11 carbon atoms, where the aryl nucleus may be unsubstituted or mono-substituted by alkyl of 1 to 4 carbon atoms, hydroxyl, methoxy, amino, acetylamino, nitro, carboxyl, cyclohexyl, phenyl, or halogen, and a mono-substituted phenyl moiety may, in addition, be mono- or di-substituted by alkyl of 1 to 4 carbon atoms, halogen, or both, where said substituents on the phenyl moiety may be identical or different from each other; triphenylmethyl; N-methyl-cyclohexylamino-carbonylmethyl; amino-iminomethyl; pyridyl; pyridylmethyl; furfuryl; benzimidazolyl; benzthiazolyl; pyrimidyl; 1,2,4-triazolyl; quinolyl; quinazoline-4-one-yl; 4,5-bis-(p-chlorphenyl)-oxazole-2-yl; pyridyl-oxide; methylpyridyl; methoxypyridyl; fluoropyridyl; chloropyridyl; aminopyridyl; acetylaminopyridyl; or, when m is 1 or D is hydroxyalkylene or xylylene, also alkyl of 1 to 6 carbon atoms; and $R_3$ and $R_4$ are each hydrogen, halogen, alkyl of 1 to 4 carbom atoms, amino, acetylamino or nitro.

2. A compound of claim 1, wherein

W is vinylene, methyl-vinylene, or ethylene;

m is 0, 1 or 2;

D is straight or branched alkylene of 2 to 6 carbon atoms, straight or branched hydroxy-alkylene of 3 to 6 carbon atoms, or xylylene;

$R_1$ is hydrogen or alkyl of 1 to 3 carbon atoms;

$R_2$ is cyclohexyl, benzyl, naphthyl, pyridyl, pyrimidyl, 1,2,4-triazolyl, pyridyl-oxide, furfuryl, triphenylmethyl, quinolyl, benzimidazolyl, benzthiazolyl, quinazoline-4-one-yl, 4,5-bis(p-chlorophenyl)-oxazol-2-yl, N-methyl-cyclohexylamino-carbonylmethyl, amino-iminomethyl, phenyl unsubstituted or substituted by carboxyl, hydroxyl, methoxy, amino, acetylamino, nitro, cyclohexyl or phenyl; phenyl mono- or disubstituted by halogen and/or alkyl of 1 to 4 carbon atoms; or hydroxyphenyl, halophenyl or aminophenyl, each substituted by two halogen atoms or by two alkyl groups of 1 to 4 carbon atoms;

$R_3$ is hydrogen, chlorine, bromine, methyl, amino, acetylamino or nitro; and $R_4$ is hydrogen.

3. A compound of claim 1 wherein

W is vinylene, methyl-vinylene or ethylene;

m is 0, 1 or 2;

D is alkylene of 2 to 5 carbon atoms or hydroxyalkylene of 3 to 5 carbon atoms;

$R_1$ is hydrogen;

$R_2$ is cyclohexyl, phenyl, benzyl, naphthyl, biphenylyl, cyclohexylphenyl, pyridyl, methylphenyl, methoxyphenyl, fluorophenyl, chlorophenyl, dichlorophenyl, trichlorophenyl, bromophenyl, dibromophenyl, bromomethylphenyl, amino-dibromophenyl or hydroxy-ditert.butylphenyl; and $R_3$ and $R_4$ are each hydrogen.

4. A compound of claim 1 wherein

W is ethylene, vinylene or 2-methylvinylene;

m is 0, 1 or 2;

$R_2$ is cyclohexyl, phenyl, benzyl, naphthyl-(2), 2-methoxyphenyl, 4-chlorophenyl, 3,4-dichlorophenyl, 2,5-dichlorophenyl, 4-hydroxy-3,5-di-tert.butylphenyl, 4-amino-3,5-dibromophenyl or pyridyl-(2);

D is ethylene, n-propylene, n-butylene or 2-hydroxy-n-propylene; and $R_1$, $R_3$ and $R_4$ are each hydrogen.

5. The compound of claim 4, which is 6-(4-phenylsulfinyl-butoxy)-3,4-dihydro-carbostyril.

6. The compound of claim 4, which is 6-[4-(3,4-dichlorophenyl-sulfinyl)-butoxy]-3,4-dihydro-carbostyril.

7. The compound of claim 4, which is 6-[4-(2-pyridyl-sulfonyl)-butoxy]-carbostyril.

8. A cardiotonic or antithrombotic pharmaceutical dosage unit composition consisting essentially of an inert pharmaceutical carrier and an effective cardiotonic or antithrombotic amount of a compound of claim 1.

9. The method of increasing the strength of the heart muscle contraction or preventing or relieving thrombosis in a warm-blooded animal in need of such treatment, which comprises perorally, parenterally or rectally administering to said animal an effective cardiotonic or antithrombotic amount of a compound of claim 1.

* * * * *

UNITED STATES PATENT AND TRADEMARK OFFICE
CERTIFICATE OF CORRECTION

PATENT NO. : 4,329,347

DATED : May 11, 1982

INVENTOR(S) : ERICH MÜLLER ET AL.

It is certified that error appears in the above—identified patent and that said Letters Patent is hereby corrected as shown below:

Title page, 10th line from bottom of Abstract:

"heteroarlkyl" should read -- heteroaralkyl --.

Column 1, line 51: "hydrox-" should read -- hydroxy- --.

Column 1, line 52: "yalkylene" should read -- alkylene --.

Column 7, lines 43 and 59; Column 41, line 52; Column 44, lines 51 and 53:

"butox-" should read -- butoxy]- --.

Column 7, lines 44 and 60; Column 27, line 54; Column 41, line 53; Column 44, lines 52 and 54

Delete "y]-".

Column 10, line 26: "6-[4-(2:" should read -- 6-[4-(2- --.

Column 11, line 36: "thi-" should read -- thio- --.

Column 11, line 37: "ophenol" should read -- phenol --.

Column 17, line 39: "slica" should read -- silica --.

Column 18, line 44: "chloroe-" should read -- chloro- --.

Column 18, line 45: "thoxy" should read -- ethoxy --.

Column 25, line 23: "6:[4-" should read -- 6-[4- --.

Column 26, line 53: "6-(b 4-" should read -- 6-(4- --.

Column 26, line 64: "3,5di-tert." should read -- 3,5-di-tert. --.

Column 27, line 7: "dihyldro" should read -- dihydro --.

Column 27, line 53: "propox-" should read -- propoxy]- --.

UNITED STATES PATENT AND TRADEMARK OFFICE
CERTIFICATE OF CORRECTION

PATENT NO. : 4,329,347
DATED : May 11, 1982
INVENTOR(S) : ERICH MÜLLER ET AL.

It is certified that error appears in the above—identified patent and that said Letters Patent is hereby corrected as shown below:

Column 32, line 40: "6[4-" should read -- 6-[4-(4- --.
Column 32, line 57: "Examples" should read -- Example --
Column 33, line 67: "carbosty-ril" should read
                          -- carbostyril --.
Column 46, line 24: "Lehrbuck" should read -- Lehrbuch --.
Column 49: Correct TABLE VII to read:

-- TABLE VII

Percent Reduction in the Number of Thrombocytes
After Intravenous Administration of Tumor Cells

|  |  | n | % Reduction of the Number of Thrombocytes |
|---|---|---|---|
| Control |  | 14 | 70 |
| Substance | Dose (mg/kg) |  |  |
| T | 2 | 22 | 29 |
|  | 4 | 28 | 15 |
|  | 8 | 30 | 1.1 |
| U | 2 | 18 | 34 |
|  | 6 | 26 | 20.8 |
|  | 18 | 30 | 1.1 |

--

UNITED STATES PATENT AND TRADEMARK OFFICE
CERTIFICATE OF CORRECTION

PATENT NO. : 4,329,347

DATED : May 11, 1982

INVENTOR(S) : ERICH MÜLLER ET AL.

It is certified that error appears in the above—identified patent and that said Letters Patent is hereby corrected as shown below:

Column 50, line 47: "Polyvinylpurrolidone" should read
-- Polyvinylpyrrolidone --.

Column 51, lines 23 and 44: "compouned" should read
-- compounded --.

Column 54, lines 23/24: "hydrox-pyropylmethylcellulose" should read
-- hydroxy-propylmethylcellulose --.

Signed and Sealed this

Twenty-third Day of November 1982

[SEAL]

Attest:

Attesting Officer

GERALD J. MOSSINGHOFF

Commissioner of Patents and Trademarks